United States Patent
Koenderman et al.

(10) Patent No.: US 8,460,883 B2
(45) Date of Patent: Jun. 11, 2013

(54) ACTIVATION EPITOPE OF FCγRII (CD32), BINDING MOLECULES THAT SPECIFICALLY BIND THE EPITOPE AND MEANS AND METHODS FOR THE DETECTION OF THE EPITOPE, AND USES OF SAID EPITOPE OR SAID BINDING MOLECULES

(75) Inventors: Leendert Koenderman, Maartensdijk (NL); Deonysius Huibert Adrianus Johannes Kanters, Schuinesloot (NL); Johannes Antonius Maria Raaijmakers, Vianen (NL); Louis Petrus Hendrikus Leenen, Utrecht (NL)

(73) Assignee: UMC Utrecht Holding B.V., Utrecht (NL)

( * ) Notice: Subject to any disclaimer, the term of this patent is extended or adjusted under 35 U.S.C. 154(b) by 518 days.

(21) Appl. No.: 12/520,852

(22) PCT Filed: Dec. 21, 2007

(86) PCT No.: PCT/NL2007/050699
§ 371 (c)(1),
(2), (4) Date: Oct. 28, 2009

(87) PCT Pub. No.: WO2008/075962
PCT Pub. Date: Jun. 26, 2008

(65) Prior Publication Data
US 2010/0047250 A1 Feb. 25, 2010

(30) Foreign Application Priority Data
Dec. 21, 2006 (EP) .................................. 06077299

(51) Int. Cl.
*G01N 33/53* (2006.01)

(52) U.S. Cl.
USPC ......................................................... 435/7.1

(58) Field of Classification Search
None
See application file for complete search history.

(56) References Cited

FOREIGN PATENT DOCUMENTS
WO   WO-02/074789   9/2002

OTHER PUBLICATIONS

Babcock, Cytometry Part B (Clinical Cytometry) (2003) 53B:48-53.
Brooki et al., Polski Przeglad Chirurgiczny (2004) 76(8):799-808.
Fjaertoft et al., Scandinavian Journal of Infectious Diseases (2007) 39(6-7):525-535.
Holzer et al., European Surgical Research (2002) 34(2):275-284.
International Search Report for PCT/NL2007/050699, mailed on Apr. 23, 2008, 6 pages.
Koenderman et al., Journal of Leukocyte Biology (2000) 68:58-64.
Luijk et al., Journal of Allergy and Clinical Immunology (2005) 115(5):997-1003.
Simms et al., Archives of Surgery (1997) 132:171-177.

*Primary Examiner* — Michail Belyavskyi
(74) *Attorney, Agent, or Firm* — Morrison & Foerster LLP

(57) ABSTRACT

The present invention provides means and method for detecting an activation epitope on FcγRII (CD32) on Fcγ (CD32) expressing cells. The presence of epitope on FcγRII (CD32) correlates with priming of the cell containing FcγRII (CD32) expressing said epitope. The invention further provides binding molecules specific for said activation epitope on FcγRII (CD32), and uses thereof in the detection of activated cells. Further uses are the treatment of individuals suffering from inflammation or at risk of suffering thereof. Also provided, among others, are uses for detecting and/or following an inflammation in an individual.

4 Claims, 32 Drawing Sheets

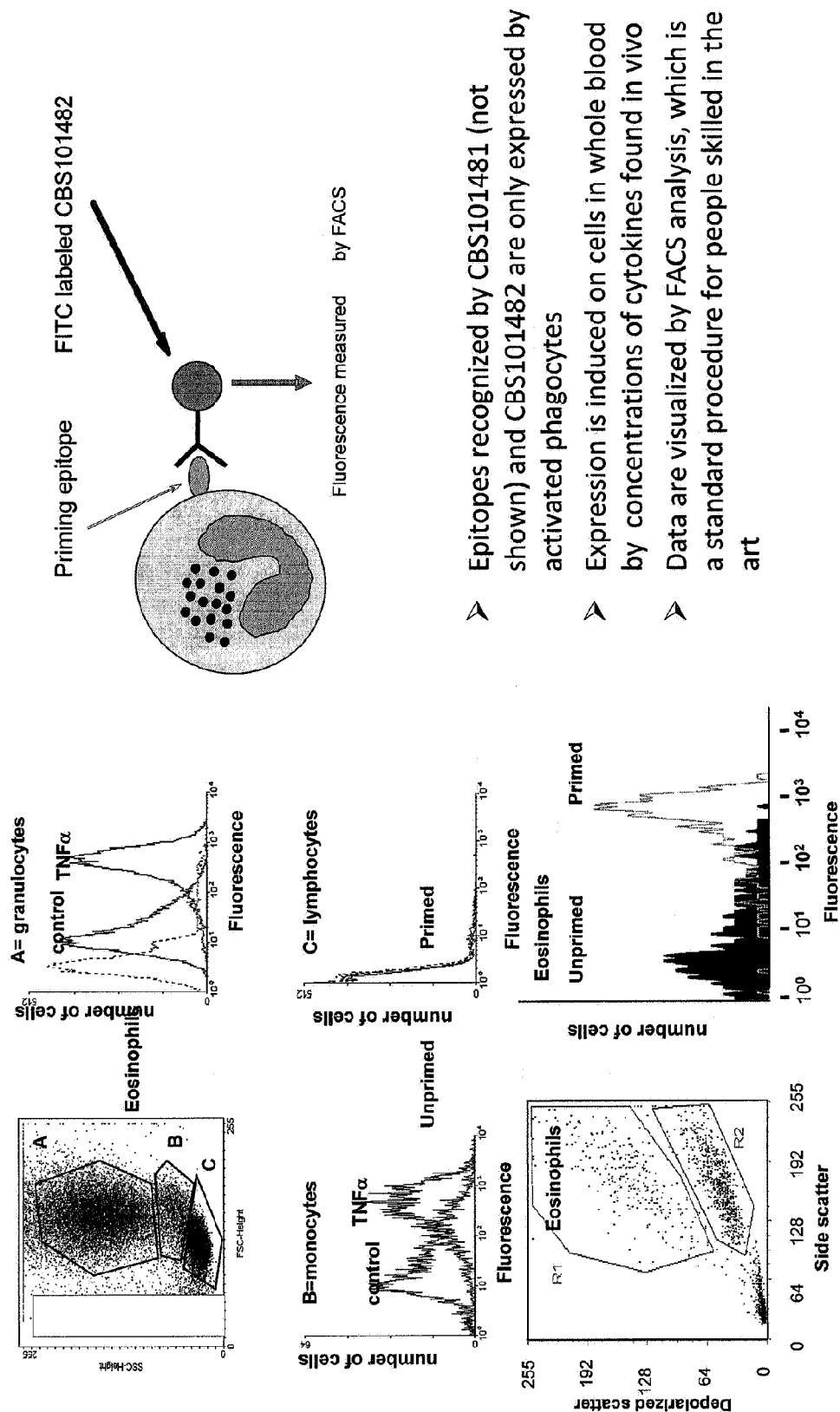
Figure 1: Methodology to measure the activation epitope present on FcγRII (CD32) on phagocytes recognized by the monoclonal phage antibodies CBS101481 (A17) and CBS101482 (A27).

Figure 2: Activation of neutrophils with inflammatory mediators induces a marked induction of expression of the activation epitope on FcγRII (recognized by CBS101481/A17)) without inducing enhancement of expression of the receptor per se Expression of the activation epitope on FcγRII (CD32) after activation of neutrophils with fMLP in the absence and presence of TNF

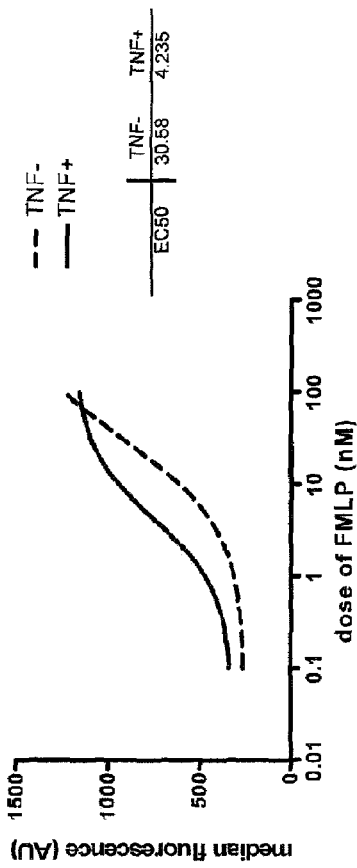

Expression of FcγRII (CD32) after activation of neutrophils with fMLP in the absence and presence of TNF

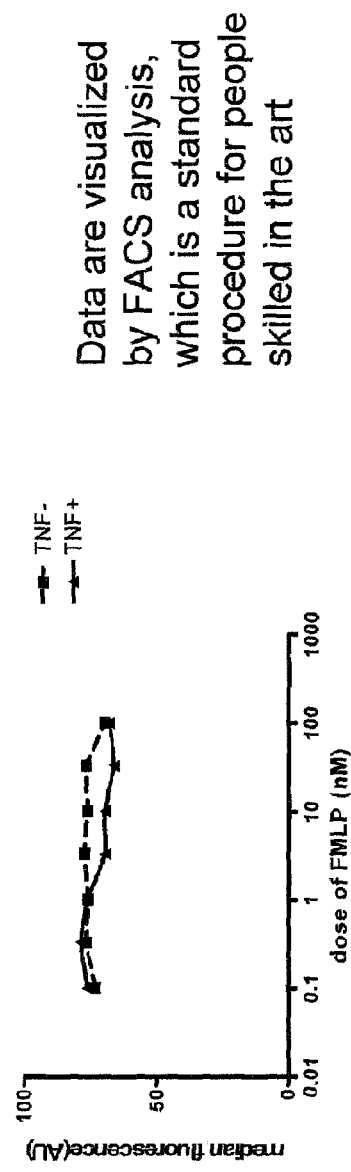

Data are visualized by FACS analysis, which is a standard procedure for people skilled in the art

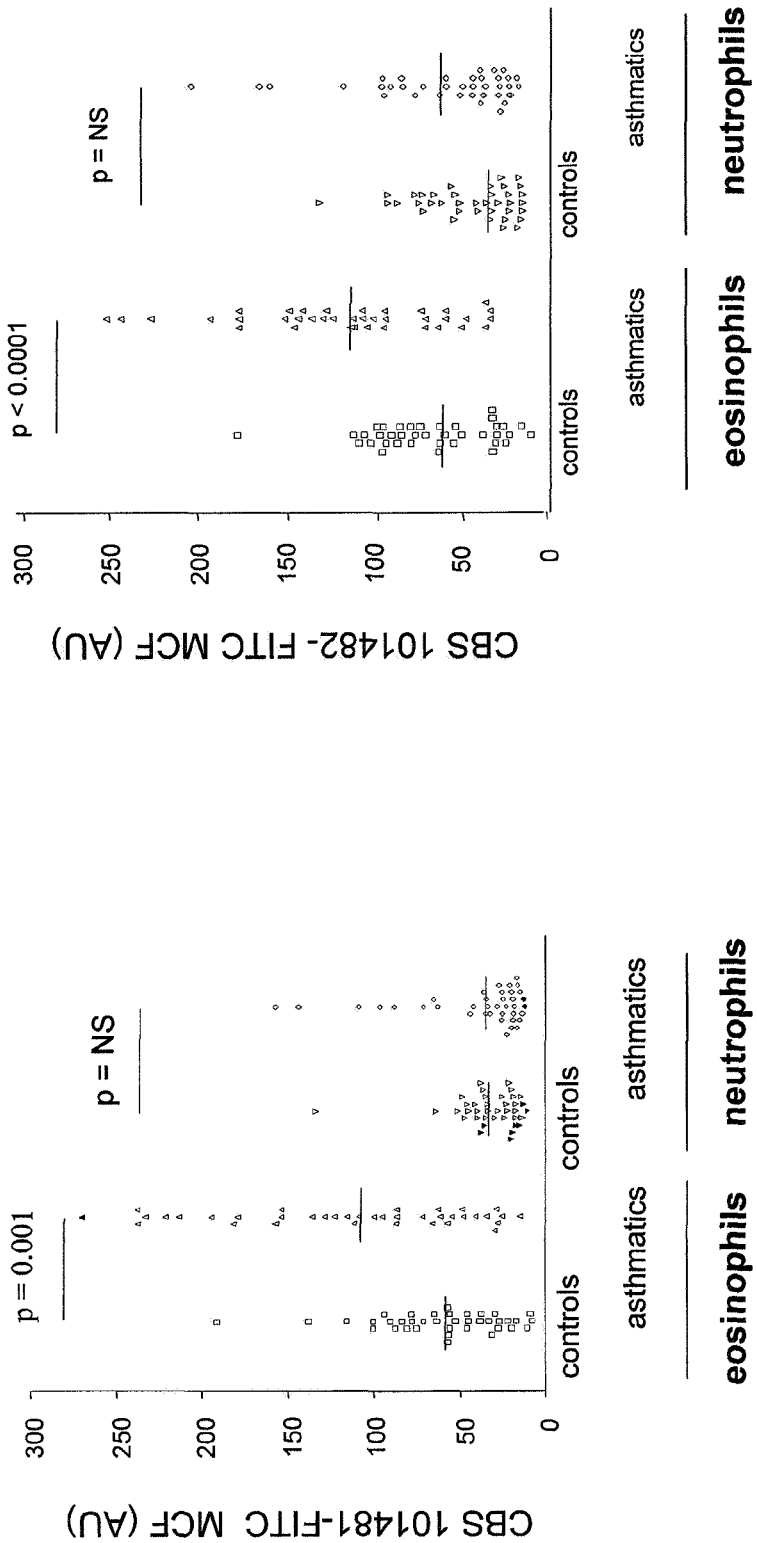
Figure 3: Patients with allergic asthma show activation of peripheral eosinophils characterized by an increase in expression of the activation epitope on FcγRII (recognized by CBS101481 and CBS101482) on peripheral blood eosinophils. This is not found for both neutrophils and eosinophils in the same blood samples.

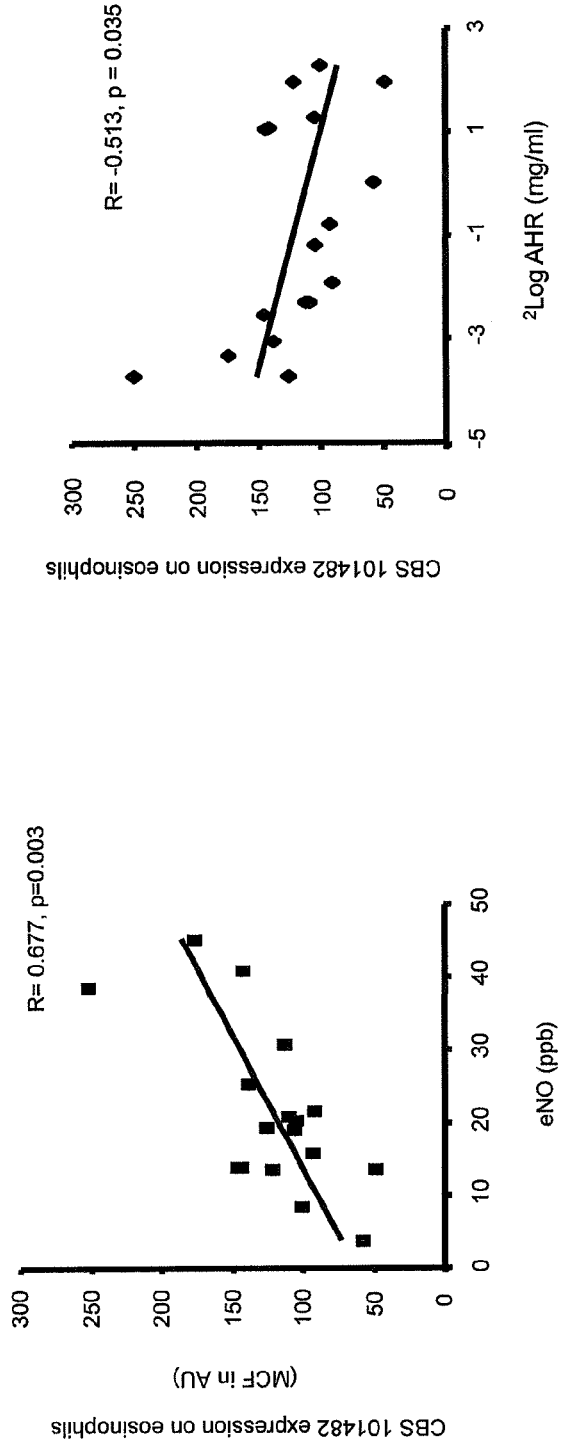

Figure 4: The severity of allergic asthma (measured by bronchial hyperresponsiveness (AHR) and exhaled NO (eNO); methods known in the art) in patients with stable disease positively correlates with the activation of peripheral eosinophils characterized by enhanced expression of the activation epitope on FcγRII (recognized by CBS101481/A17 and CBS101482/A27) on peripheral blood eosinophils. This is not found for both neutrophils and monocytes in the same blood samples. Data are visualized by FACS analysis, which is a standard procedure for people in the art, exhaled NO by a method described by (Ravensberg AJ, Luijk B, Westers P, Hiemstra PS, Sterk PJ, Lammers JW, Rabe KF. Allergy. 2006 Sep;61(9):1097-103) and bronchial hyperresponsiveness for methacholine by a standard method known for people known skilled in the art.

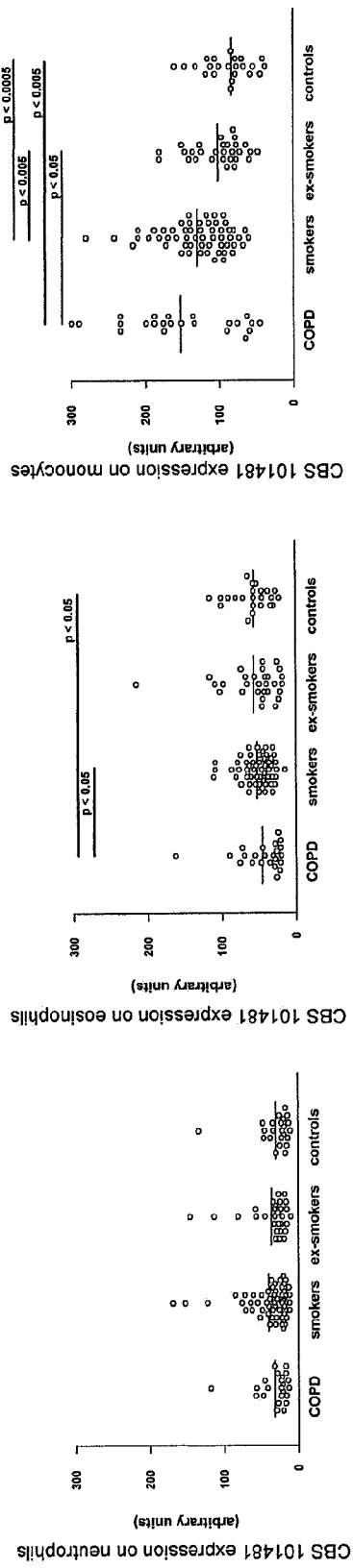

Figure 5: Individuals who actively smoke and patients with COPD show activation of peripheral monocytes characterized by increase in expression of the activation epitope on FcγRII (recognized by CBS101481/A17 and CBS101482/A27) on peripheral blood monocytes. This is not found for both neutrophils and eosinophils in the same blood samples. Data are visualized by FACS analysis, which is a standard procedure for people skilled in the art

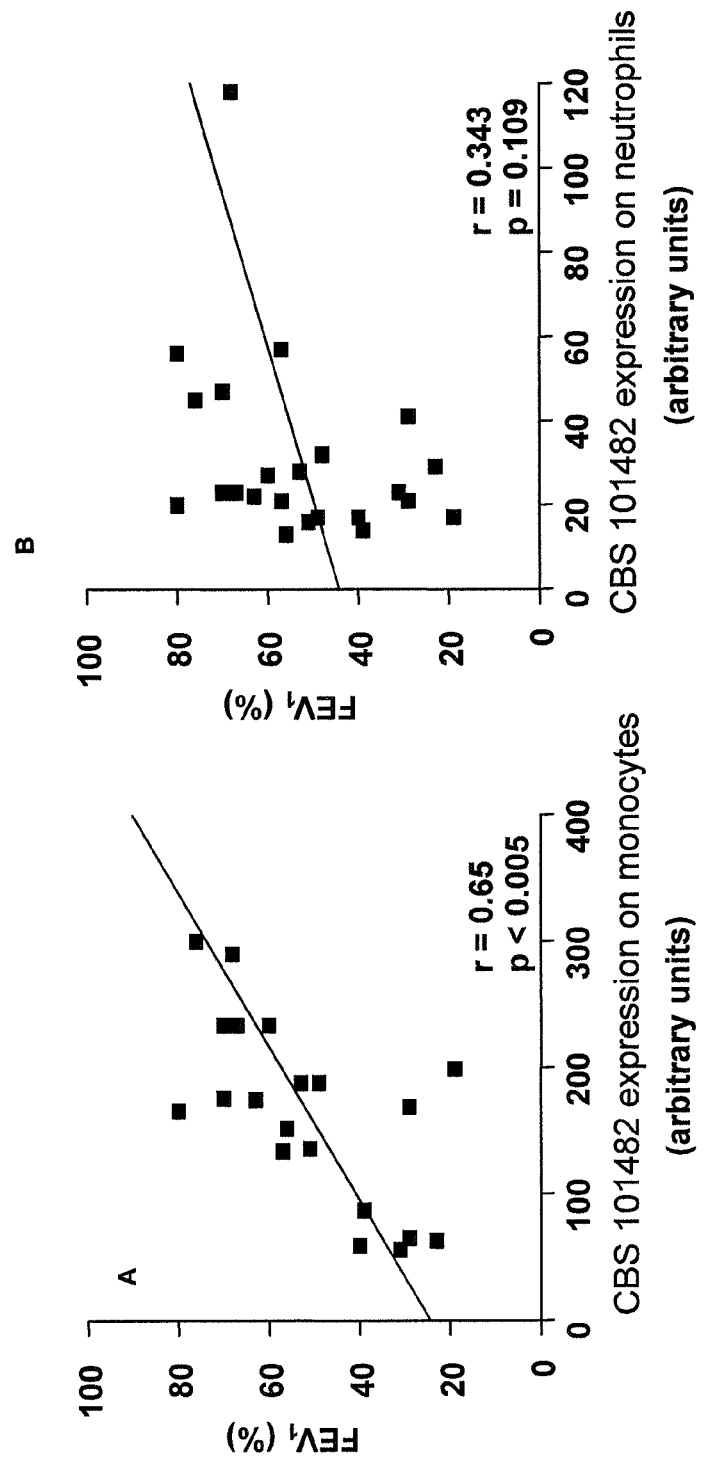

Figure 6: The severity of COPD (measured by Fev1 a method known in the art) in patients with stable disease positively correlates with the activation of peripheral monocytes characterized by enhanced expression of the activation epitope on FcγRII (recognized by CBS101481/A17 and CBS101482/A27) on peripheral blood monocytes. This is not found for both neutrophils and eosinophils in the same blood samples.

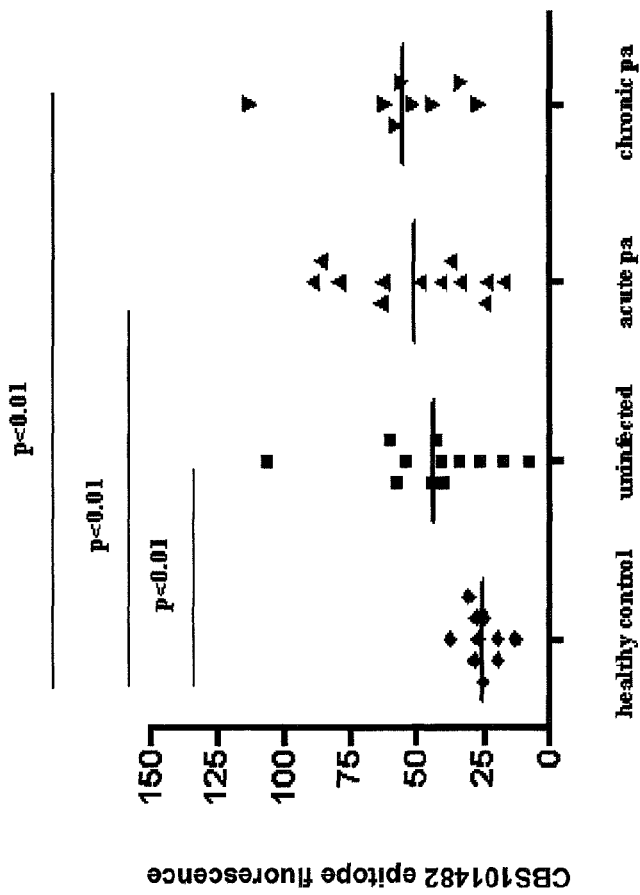

Figure 7: Disease severity in children with cystic fibrosis correlates with activation of peripheral neutrophils characterized by an increase in expression of the of the activation epitope on FcγRII (recognized by CBS101481/A17 and CBS101482/A27) on peripheral blood neutrophils. Children with cystic fibrosis are characterized by priming of peripheral blood neutrophils even in the absence of indications of colonization with pseudomonas aerigunosa (PA). During the natural course of cystic fibrosis deterioration of the diseases is accompanied by the sequential occurrence of acute or chronic colonization with PA.

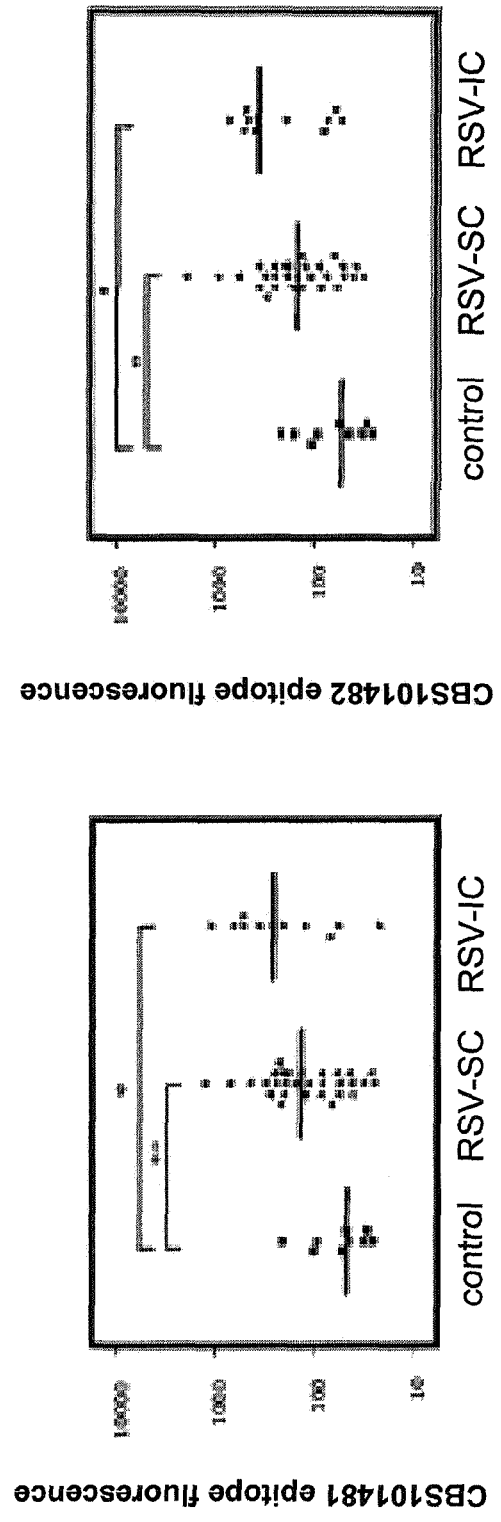

Figure 8: Disease severity in infants with RSV-induced lower respiratory tract disease as indicated by the fact that children needed standard clinical care (RSV-SC/moderate disease) or intensive care (RSV-IC/severe disease) relates to peripheral activation of eosinophils characterized by an increase in expression of the of the activation epitope on FcγRII (recognized by CBS101481/A17 and CBS101482/A27) on peripheral blood eosinophils.

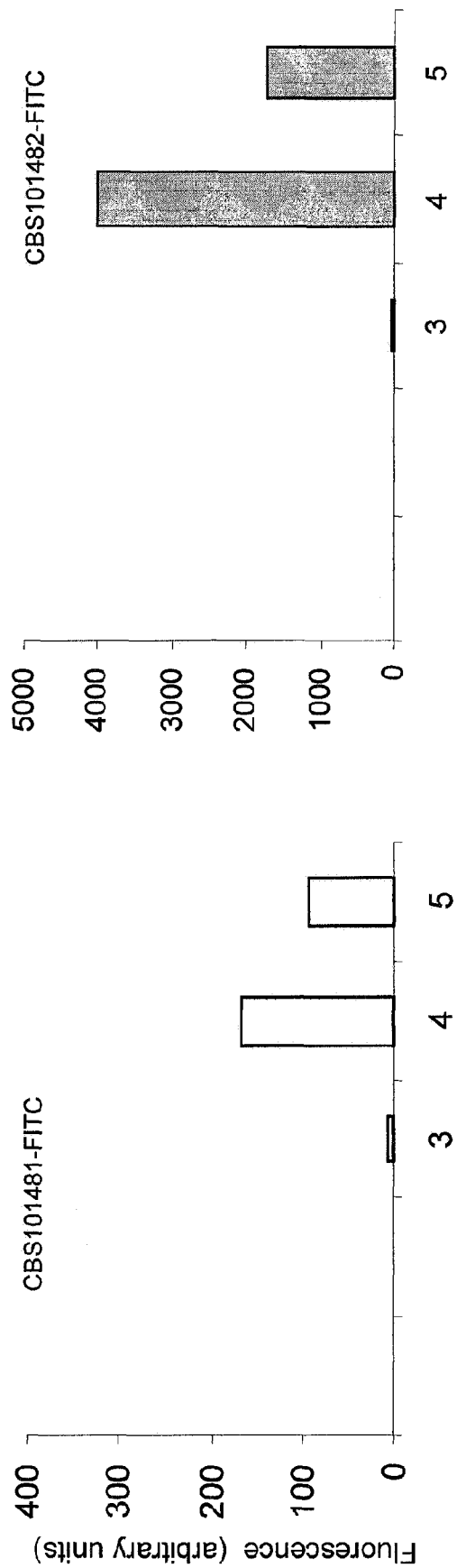

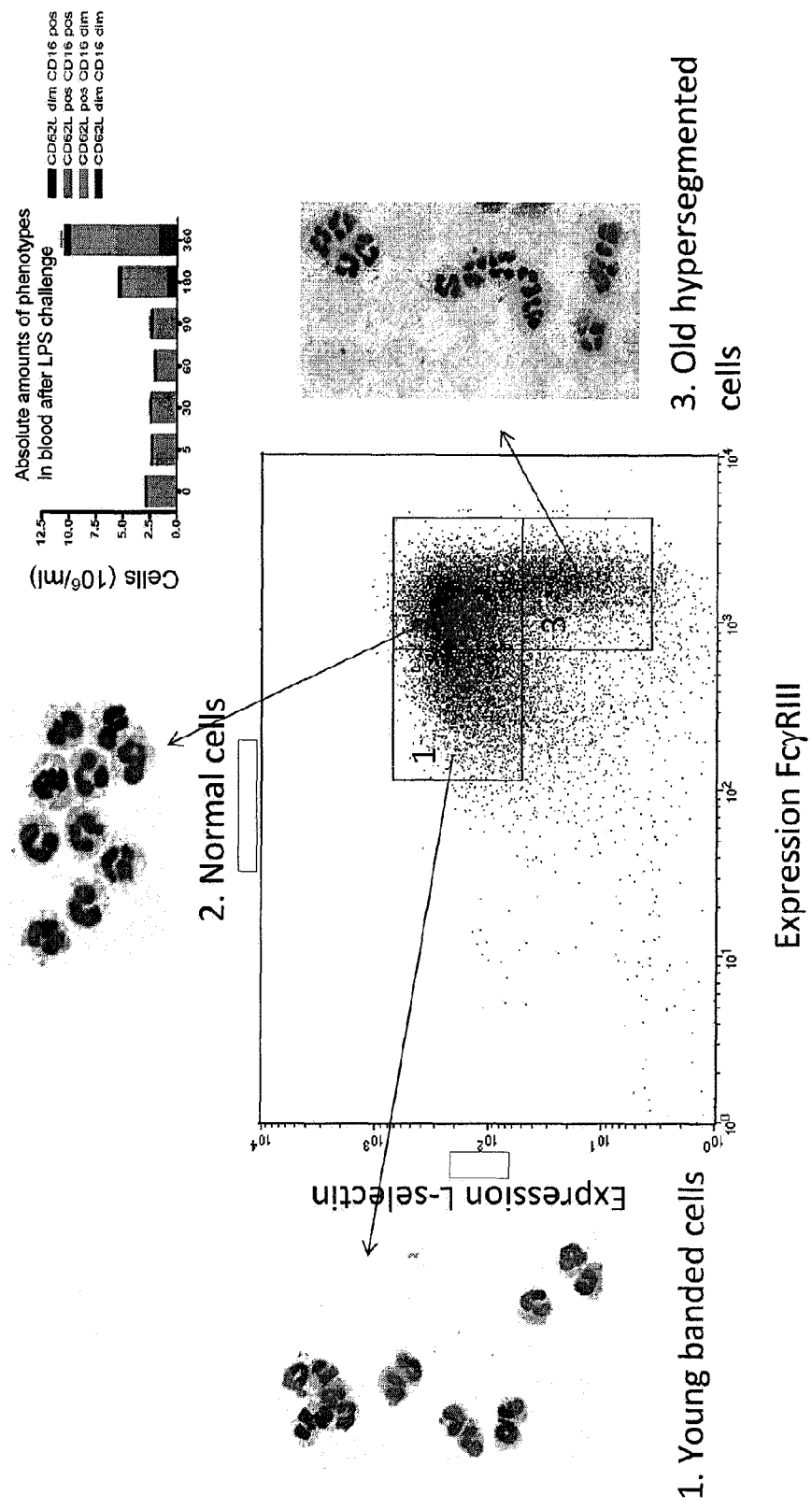

Figure 10: Blood was drawn 3 hrs after LPS challenge in normal volunteers. Hereafter, erythrocytes were lysed with ammonium chloride (Koenderman L, Kok PT, Hamelink ML, Verhoeven AJ, Bruijnzeel PL. J Leukoc Biol. 1988 Aug;44(2):79-88). Hereafter, the cells were stained with CD16/Alexa647 and CD62L/FITC for flowcytometry. Hereafter, the three populations of cells were sorted with a flowcytometer (FACSvantage) by a method known to a person known in the art.

Identification of functional neutrophil phenotypes 2
Increased expression of active FcγRII on hypersegmented cells

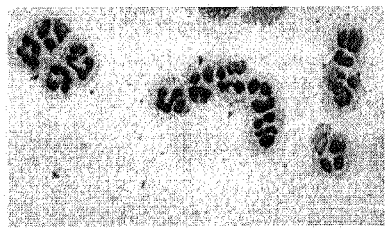

2. Normal cells

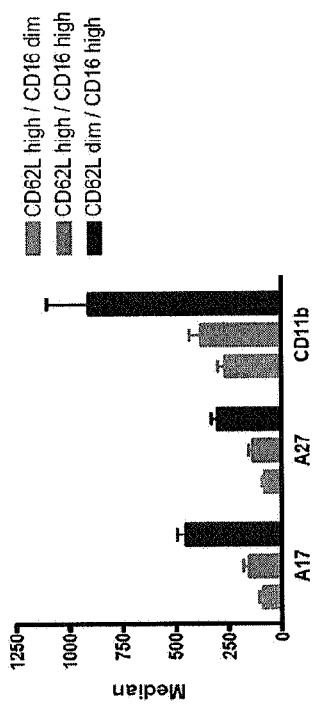

3. Old hypersegmented cells

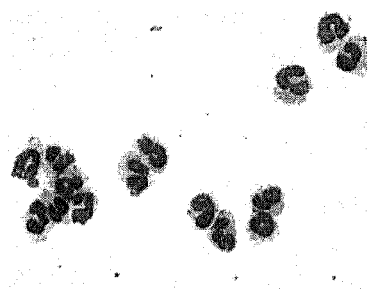

1. Young banded cells

Figure 11: Young banded and old hypersegmented cells are identifief according their CD16(Alexa 647 labeled)/CD62L (PE labeled) expression levels (see figure 10). The cells were counterstained with FITC labeled A17, A27 and CD11b.

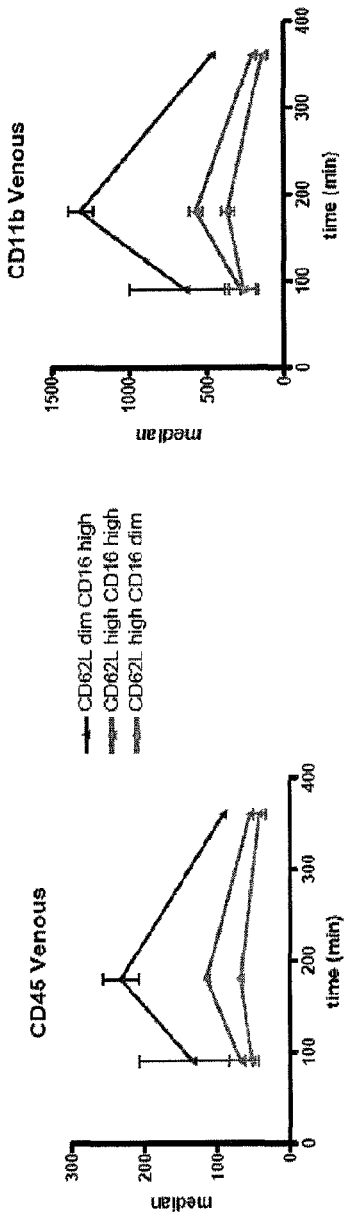
Figure 12: Young banded and old hypersegmented cells are identifier according their CD16(Alexa 647 labeled)/CD62L (PE labeled) expression levels (see figure 10). The cells were counterstained with FITC labeled CD45 and CD11b.

Identification of functional neutrophil phenotypes 3:
*The ratio of activated over non-activated expression of A17/A27 identifies refractoriness in hypersegmented cells*

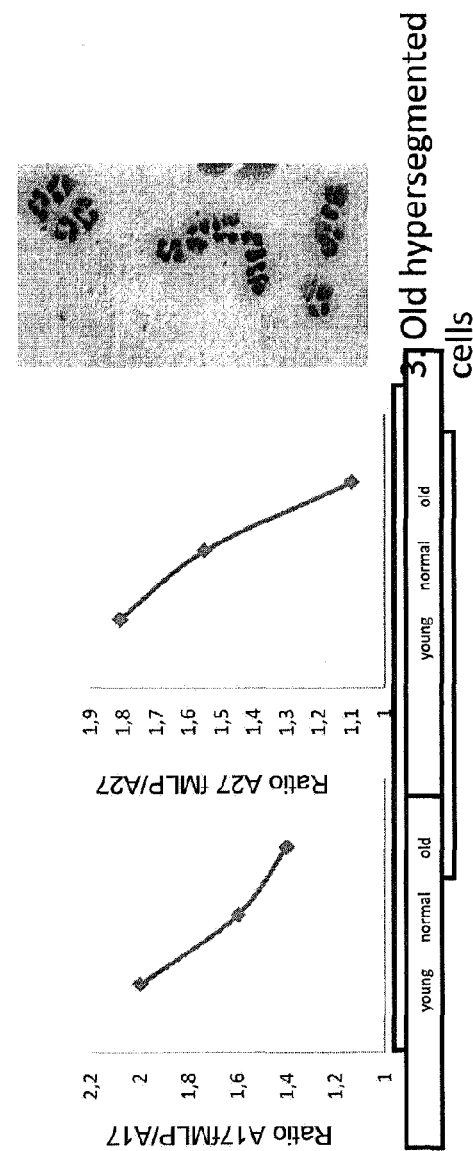

1. Young banded cells
2. Normal cells
3. Old hypersegmented cells

Figure 13 Young banded and old hypersegmented cells were isolated according their CD16(Alexa 647 labeled)/CD62L (PE labeled) expression levels (see figure 10) by cell sorting in a flowcytometer. Hereafter, cells were incubated at 37 C for 5 min in the presence and Absence of fMLP (1 µM). The quotient of expression of activated cells and resting cells identifies refractoriness

Identification of *functional* neutrophil phenotypes 1

Hypersegmented cells have upregulated cytotoxic potential

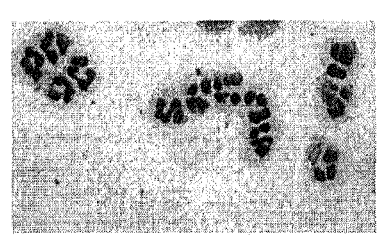

3. Old hypersegmented cells

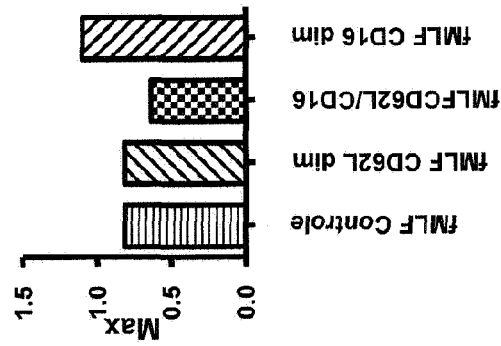

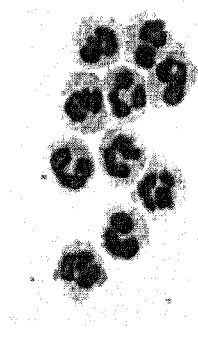

2. Normal cells

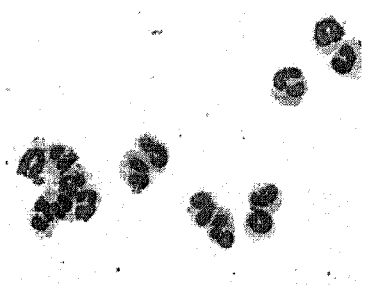

1. Young banded cells

Figure. 14: When young banded and old hypersegmented cells are isolated according to their CD16/CD62L expression levels (see figure 10). Hereafter, The cells were characterized in the context of activation of the respiratory burst. activation of the respiratory burst. The method applied is described by Kuijpers et al (Kuijpers TW, van Bruggen R, Kamerbeek N, Tool AT, Hicsonmez G, Gurgey A, Karow A, Verhoeven AJ, Seeger K, Sanal O, Niemeyer C, Roos D. Blood. 2007 Apr 15;109(8):3529-37) which measures H2O2 induced reduction of AMPLEX red in a fluorimeter as a read out for activation of the respiratory burst.

Identification of *functional* neutrophil phenotypes 1
Hypersegmented cells have suppressed chemotactic potential for C5a

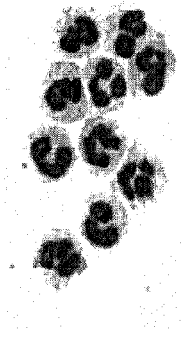

2. Normal cells

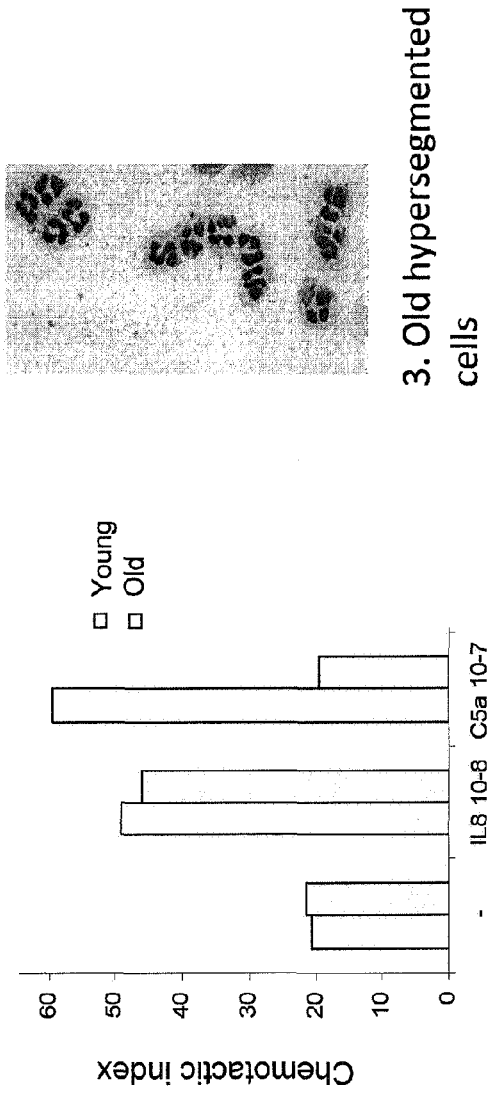

3. Old hypersegmented cells

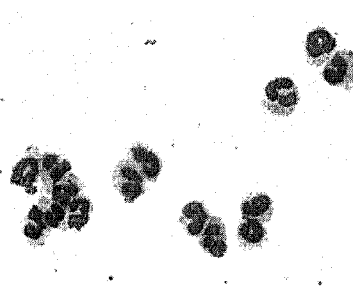

1. Young banded cells

Figure 15: When young banded and old hypersegmented cells are isolated according their CD16/CD62L expression levels (see figure 10). Hereafter, The cells were characterized in the context of activation of the respiratory burst. The method applied is described by Warringa et al. (Warringa RA, Koenderman L, Kok PT, Kreukniet J, Bruijnzeel PL. Blood. 1991 Jun 15;77(12):2694-700)

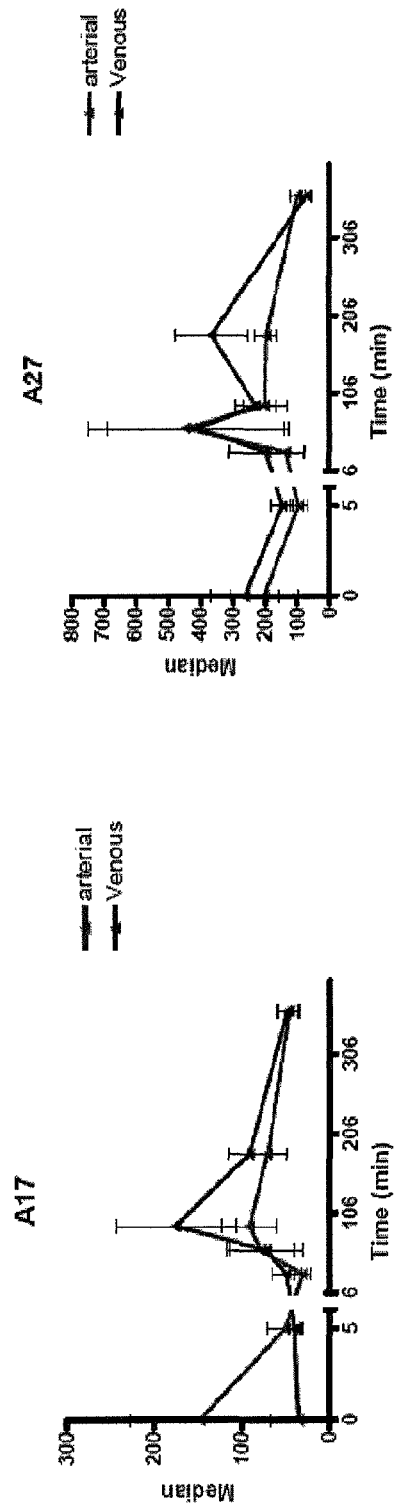
Figure 16: Blood was drawn before and on several timepoints after LPS challenge in normal volunteers. Hereafter, erythrocytes were lysed with Ammonium chloride (Koenderman L, Kok PT, Hamelink ML, Verhoeven AJ, Bruijnzeel PL. J Leukoc Biol. 1988 Aug;44(2):79-88). Hereafter, the Cells were stained with A17/FITC or A27/FITC for flowcytometry.

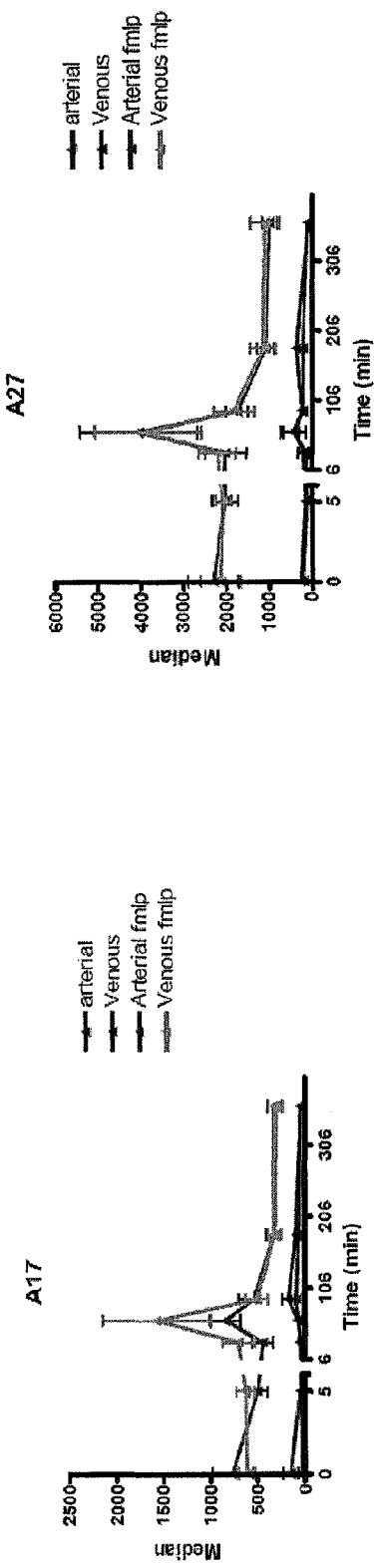
Figure 17: Blood was drawn before and on several timepoints after LPS challenge in normal volunteers. Hereafter, blood was activated with FMLP (1 μM for 5 min) before erythrocytes were lysed with Ammonium chloride (Koenderman L, Kok PT, Hamelink ML, Verhoeven AJ, Bruijnzeel PL. J Leukoc Biol. 1988 Aug;44(2):79-88). Hereafter, the cells were stained with A17/FITC or A27/FITC for flowcytometry.

Exhaustion of the innate immune system by trauma and sepsis I:

*Presence of PMNs in lung, spleen and lymph nodes while bone marrow is depleted*

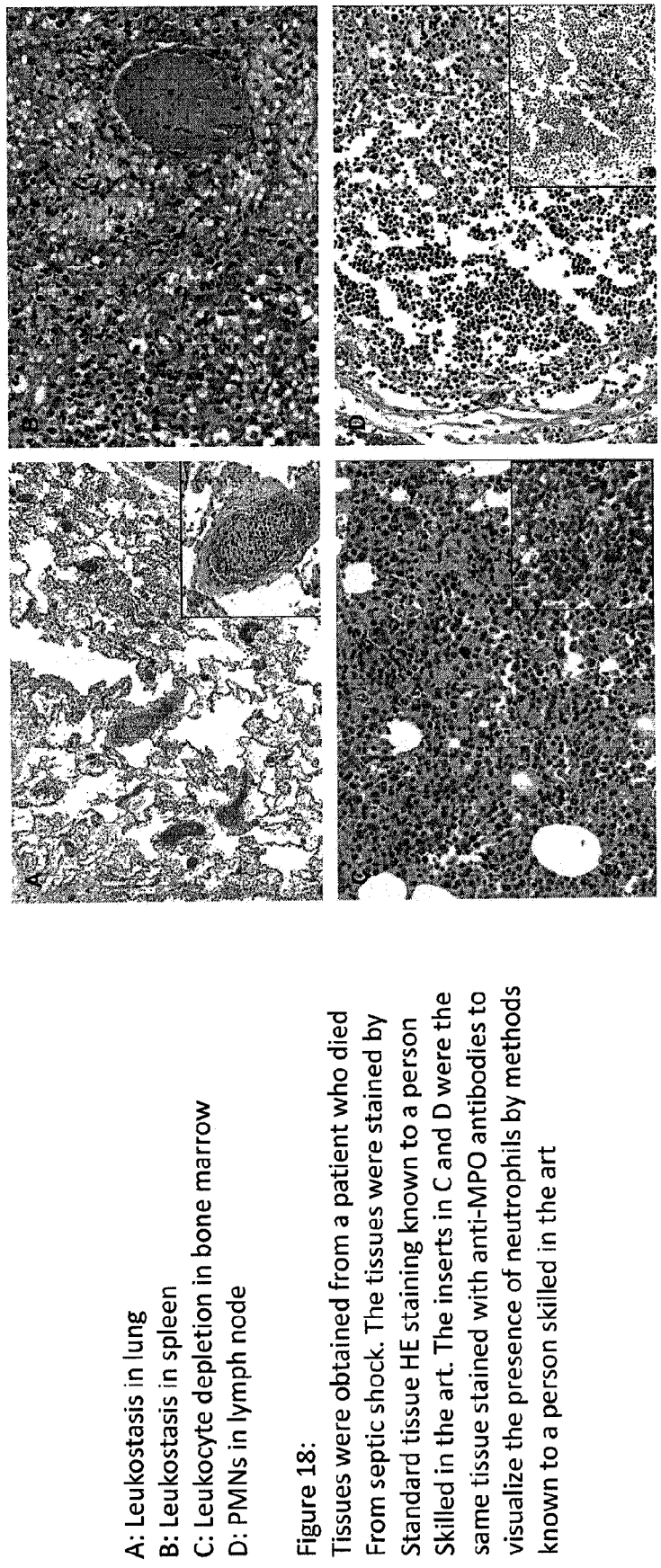

A: Leukostasis in lung
B: Leukostasis in spleen
C: Leukocyte depletion in bone marrow
D: PMNs in lymph node Figure 18:
Tissues were obtained from a patient who died from septic shock. The tissues were stained by Standard tissue HE staining known to a person skilled in the art. The inserts in C and D were the same tissue stained with anti-MPO antibodies to visualize the presence of neutrophils by methods known to a person skilled in the art

Identification of *functional* neutrophil phenotypes 1

Hypersegmented cells have upregulated suppresive function on T-cell activation

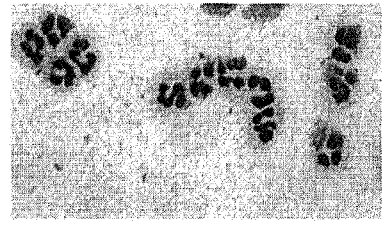

3. Old hypersegmented cells

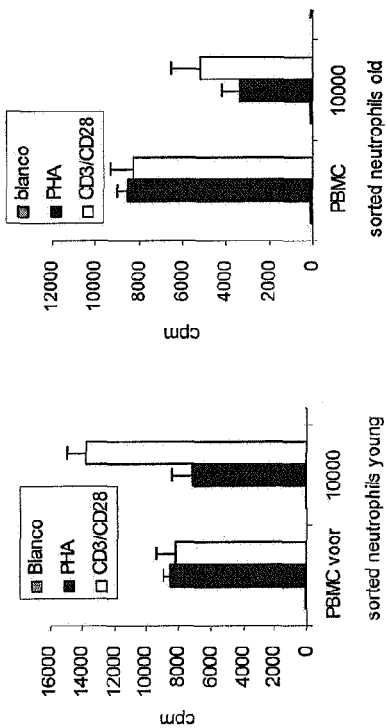

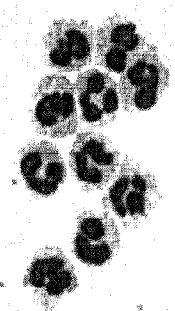

2. Normal cells

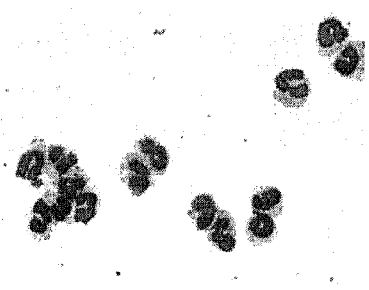

1. Young banded cells

Figure 19: When young banded and old hypersegmented cells are isolated according to their CD16/CD62L expression levels (see figure 10) cells were co-incubated with PBMC in a polyclonal T-cell activation assay for 3 days T-cell proliferation was determined by 3H-thymidine incorporation in a method known to a person skilled in the art.

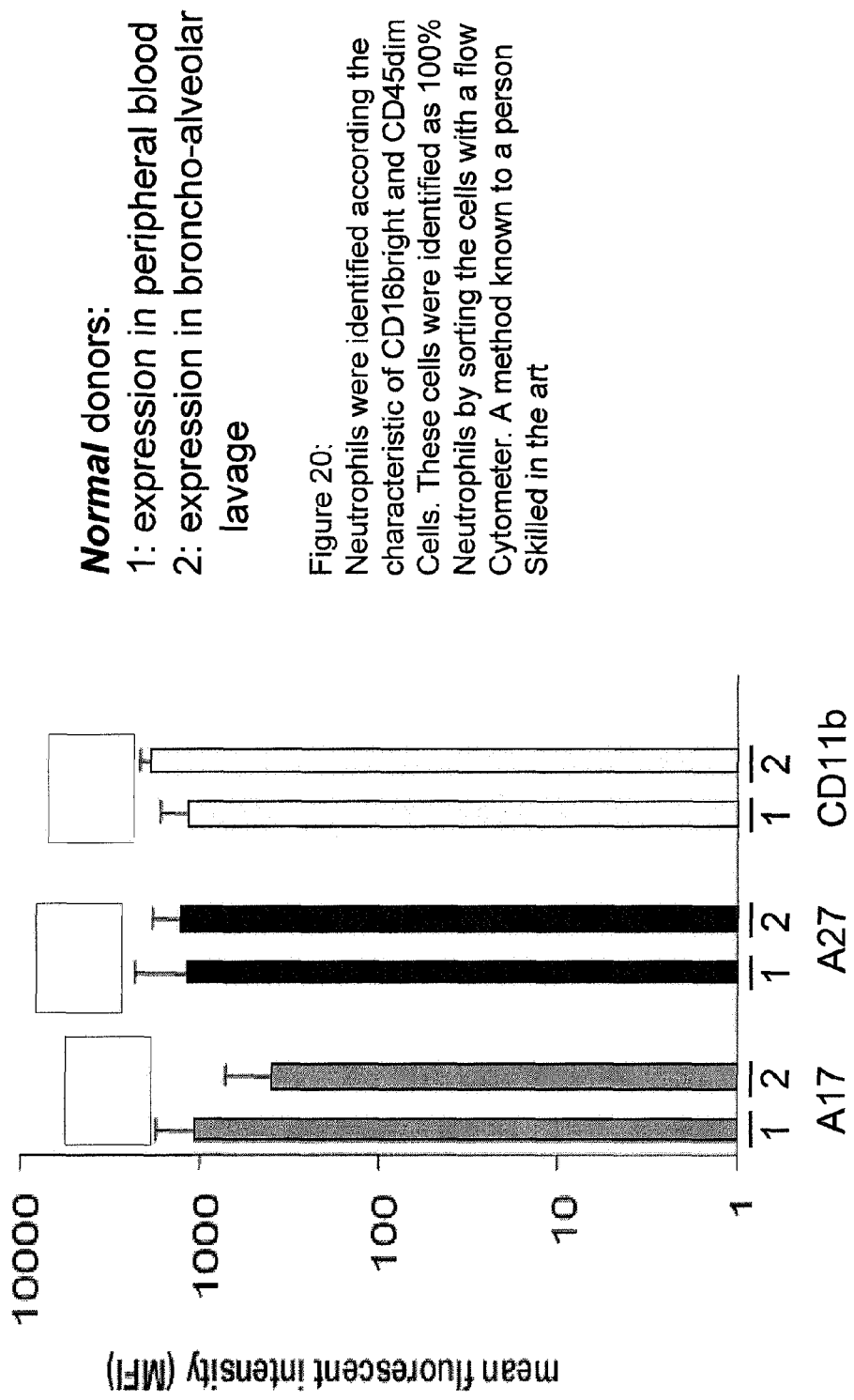

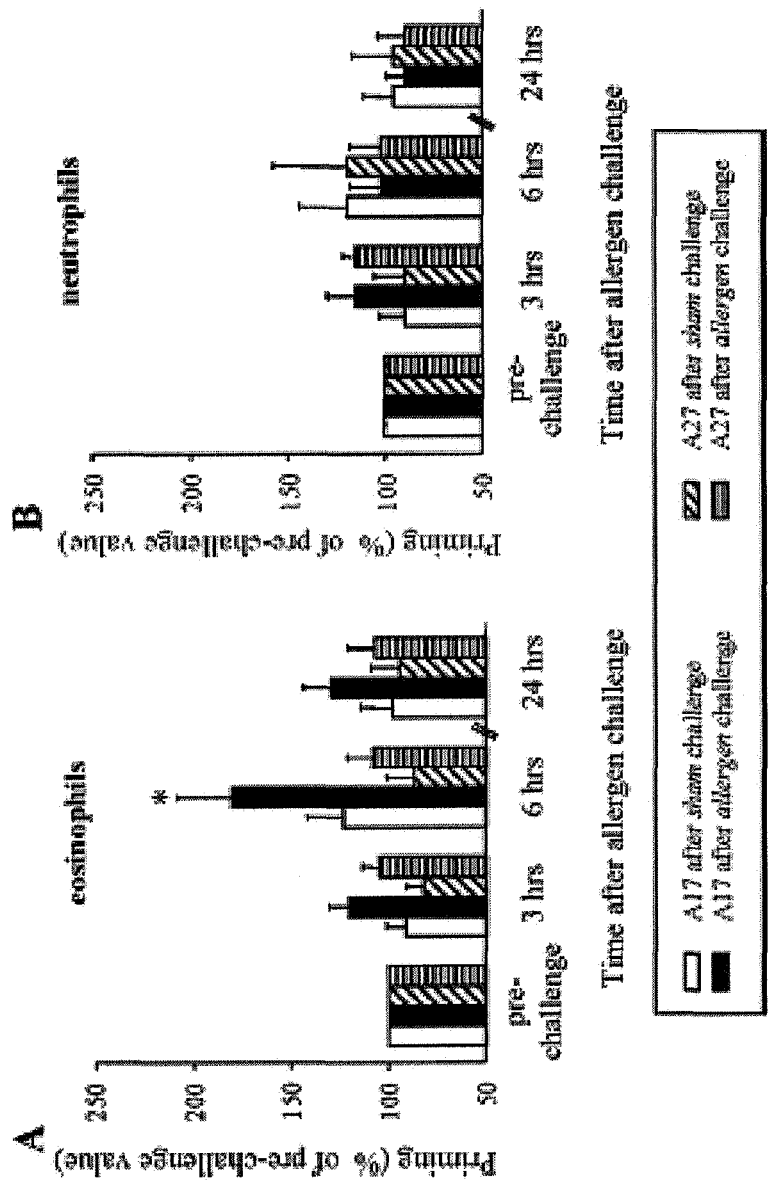
Figure 21: Kinetics of expression of priming epitopes on eosinophils in peripheral blood in response to allergen challenge in patients with asthma. The percentage change from baseline at 3, 6, and 24 hours after sham (control) or inhaled allergen challenge is expressed by MoPhab A17 and MoPhab A27 (prechallenge value set at 100%; MoPhab A17: *$P < .01$ at 6 hours).

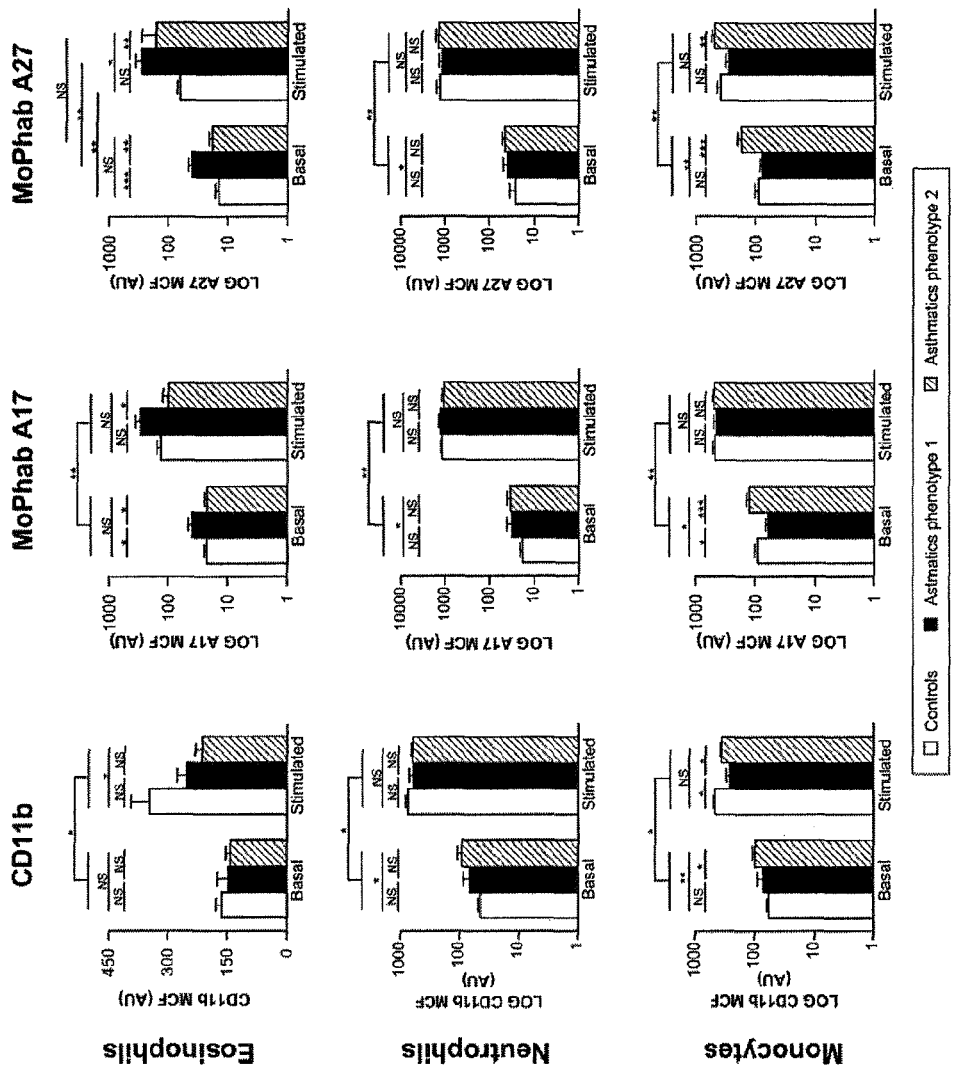

Figure 22. Priming of eosinophils, neutrophils and monocytes in mild stable asthmatics (phenotype 2), difficult-to-treat asthmatics (phenotype 1) and controls measured via cellular expression of αm (CD11b) and epitopes recognized by MoPhabs A17 and A27. Priming was measured with and without fMLP-stimulation ($10^{-6}$M). Statistics were performed using Mann-Whitney U tests (between groups) or Wilcoxon signed rank tests (between unstimulated and stimulated samples). Fluorescence (MCF) is given in arbitrary units (AU).

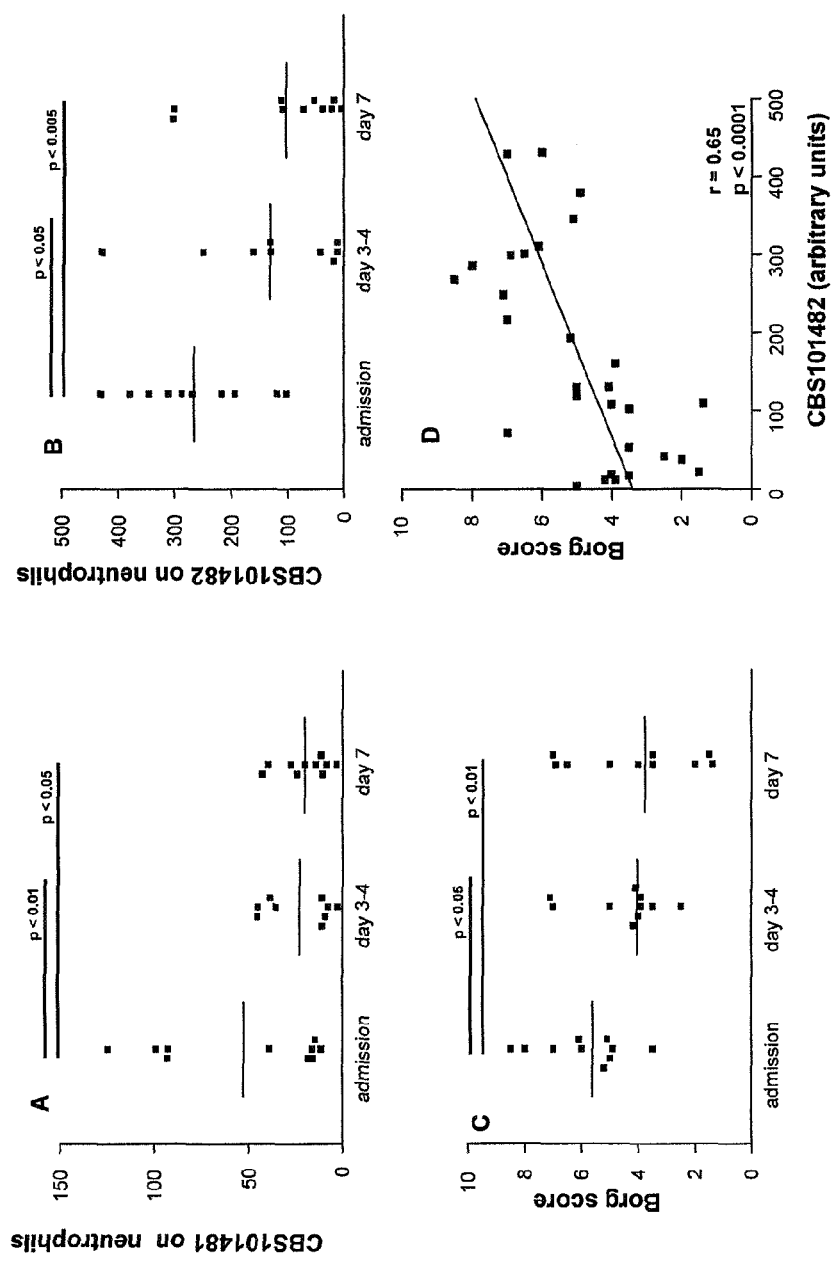

Figure 23: Resolution of disease after clinical treatment of an exacerbation of COPD is correlated with decrease in expression of the of the activation epitope on FcγRII (recognized by CBS101481/A17 and CBS101482/A27) on peripheral blood neutrophils. Disease severity of COPD was evaluated by using the dyspnea score according to Borg (known to the art). The severity of an exacerbation of COPD measured by the Borg score correlates positively with the expression of the activation epitope on FcγRII on peripheral neutrophils.

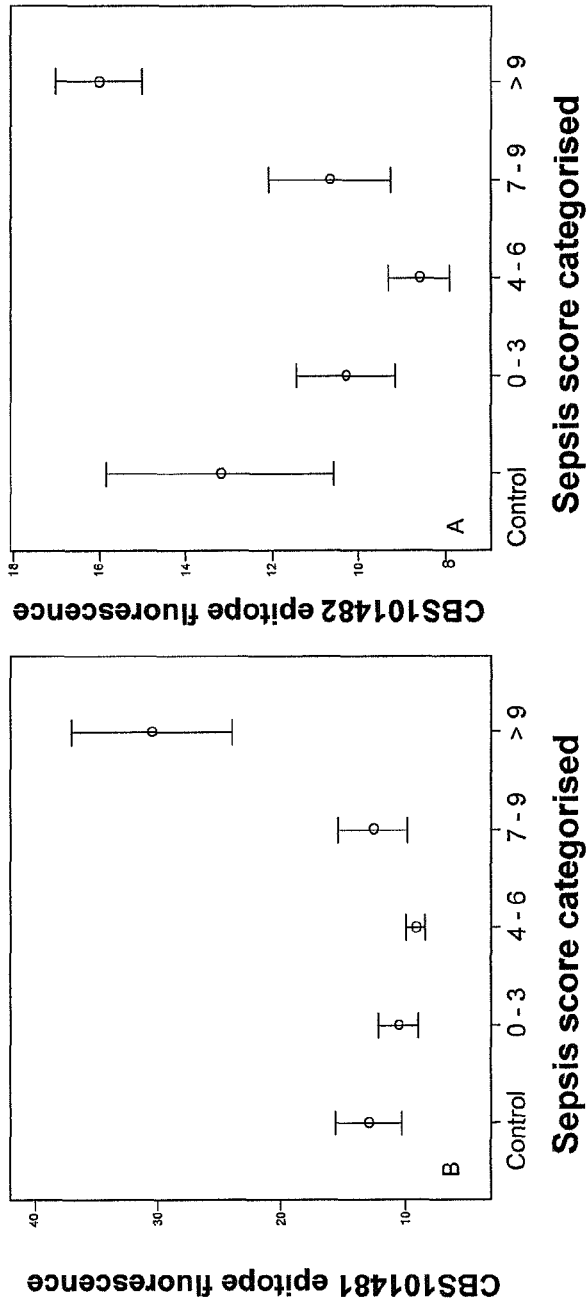
Figure 24: Disease severity in patients with multitrauma as indicated by the sepsis score (known to the art) is correlated with an increase in expression of the of the activation epitope on FcγRII (recognized by CBS101481 and CBS101482) on peripheral blood neutrophils.
Lines ⊥ represent the mean ± standard error of mean (SEM). Controls are compared with traumapatients.

Figure 25: Disease severity in patients with multitrauma as indicated by the sepsis score (known to the art) is correlated with a marked decrease in the maximal expression of the of the activation epitope on FcγRII (recognized by CBS101481/A17 and CBS101482/A27) on neutrophils as can be induced on peripheral blood neutrophils after activation of the blood with the innate immune stimulus fMLP (5 min 1μM at 37 C).

Lines ⊥ represent the mean ± standard error of mean (SEM). Controls are compared with traumapatients.

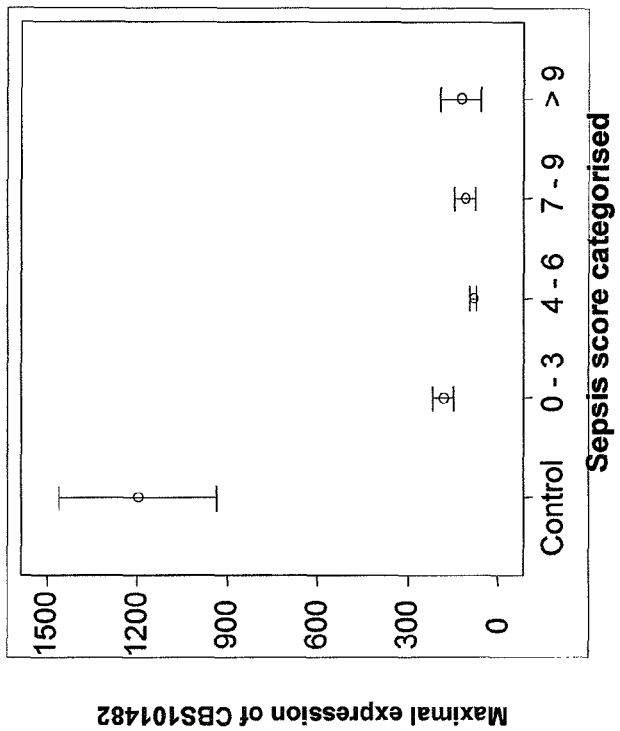

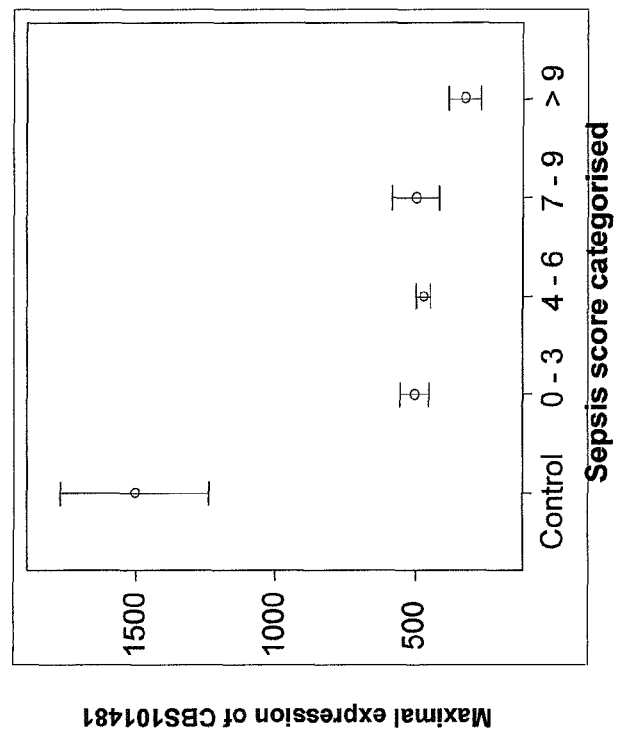

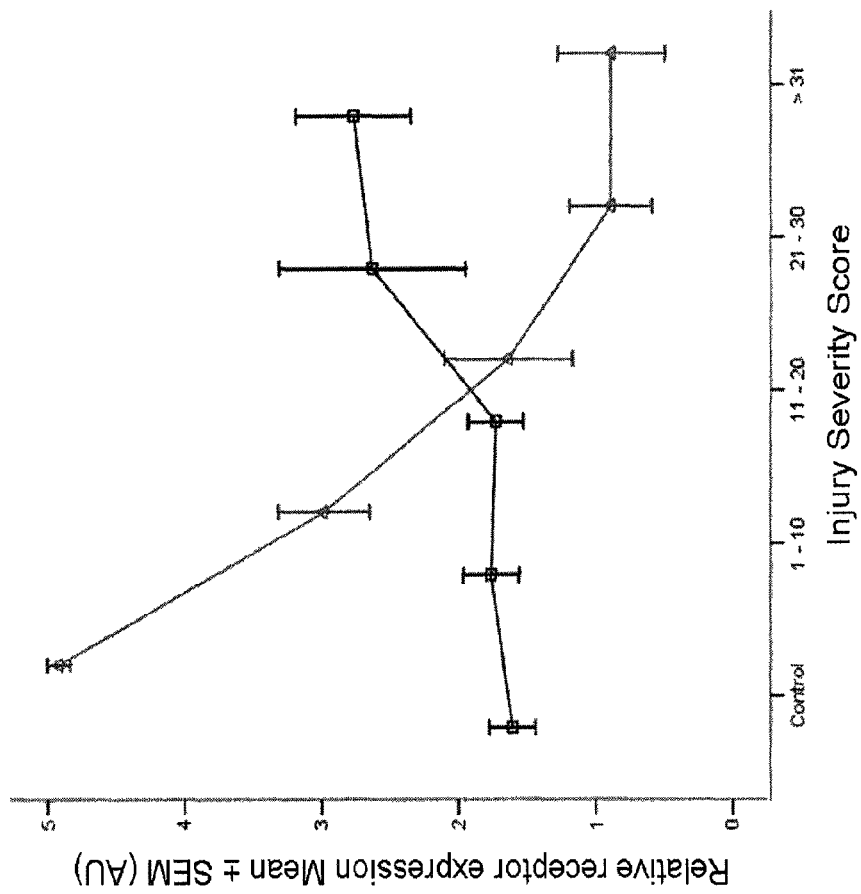

Fig. 26: Relation between CD11b and A27$_{fMLP}$ with injury severity. Figure demonstrates the relation of the injury severity, as measured by the Injury Severity Score, and the PMN surface receptors CD11b and A27 after fMLP. A reverse relation exists between CD11b and A27$_{fMLP}$. Furthermore, A27$_{fMLP}$ shows a rapid decline, even after minor injury, while CD11b increases only after severe injury. Combining these receptors creates an inflammatory score which covers the whole spectrum of injury severity.

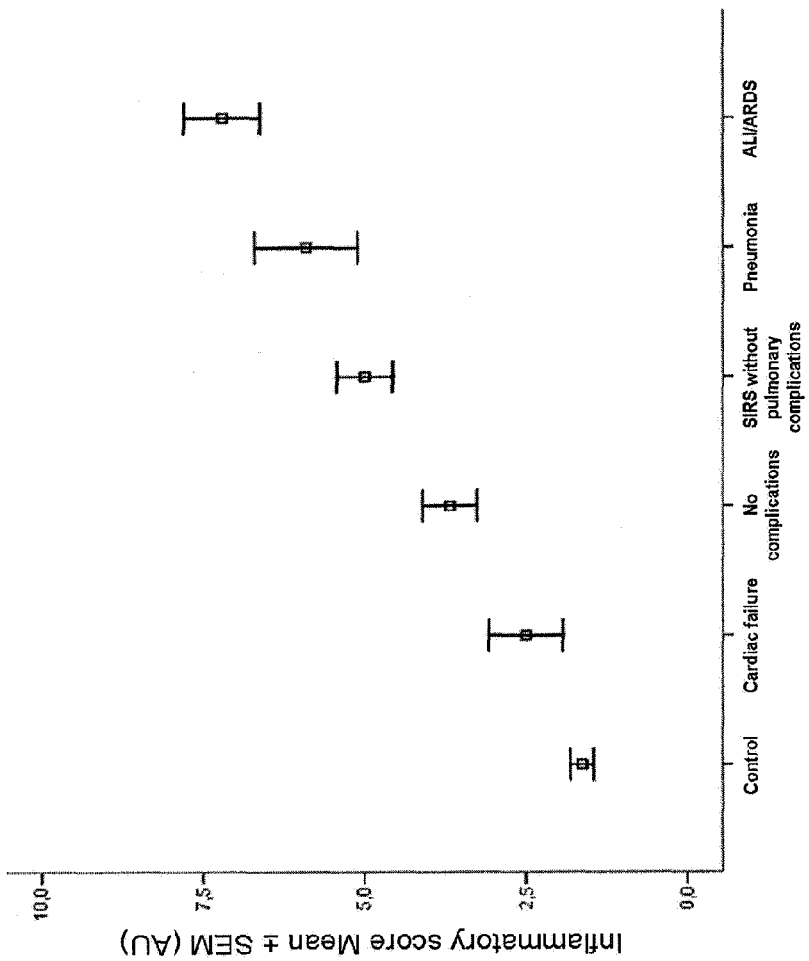

Figure 27: Relation between inflammatory score and pulmonary complications. The inflammatory score increased stepwise when the severity of complications increased in the first population cohort. Three patients with cardiac failure were depicted next to the healthy controls. This concerned elderly patients with major co-morbidities and an expected altered immune system. From the patients without complications on, the severity of inflammation increased with the severity of complications. The highest scores were found in the patients with acute lung injury or acute respiratory distress syndrome (no complications versus ALI/ARDS p = 0.001 by Mann Whitney U analysis).

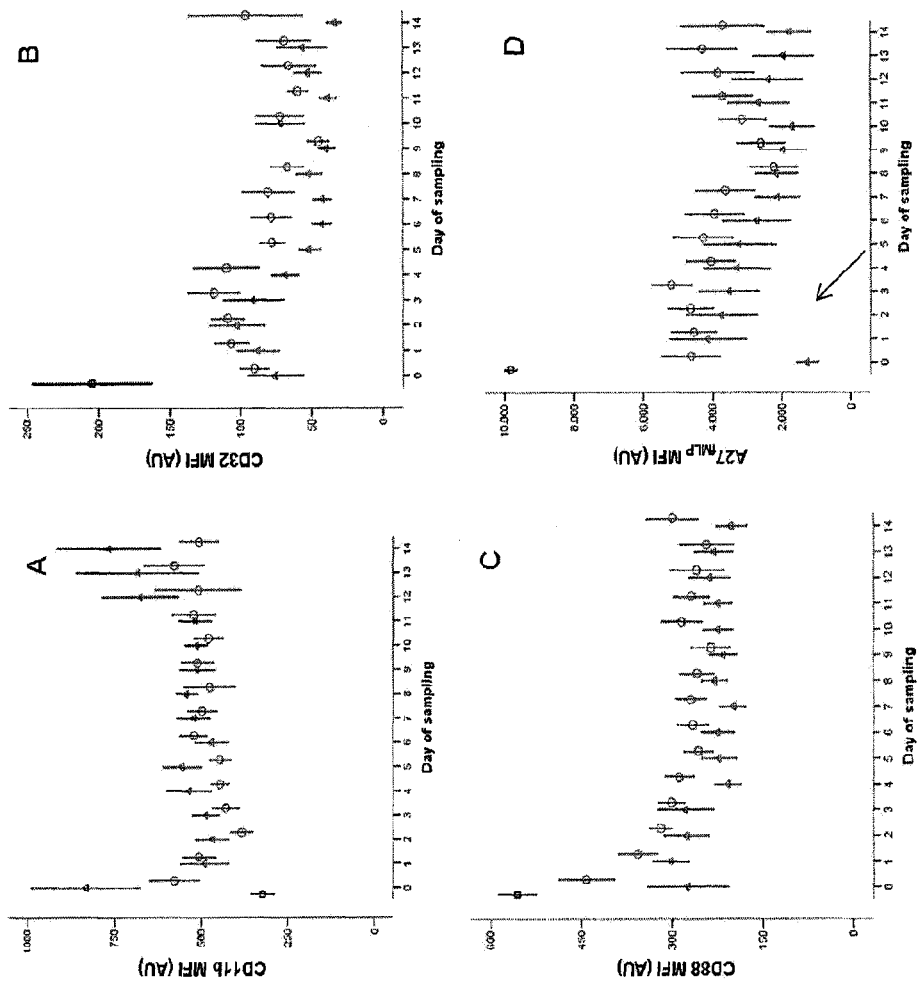

Figrue 28:
Course of PMN surface receptor expression during ICU admission.
Alterations in PMN phenotype of adhesion associated receptor (A CD11b), opsonin receptors (B CD32 and D A27$_{fMLP}$), and chemotaxis receptor (C CD88). Controls are depicted as black squares, surgical intensive care patients without septic shock during admission are depicted as green circles and patients who developed septic shock during admission are depicted as red triangles. Bars represent mean ± standard error of mean. All receptors (except CD11b) show a biphasic; after their initial decrease they improve slightly before they decrease again. CD11b is increased initially, returns to slightly above normal and increases only again after septic shock has established.

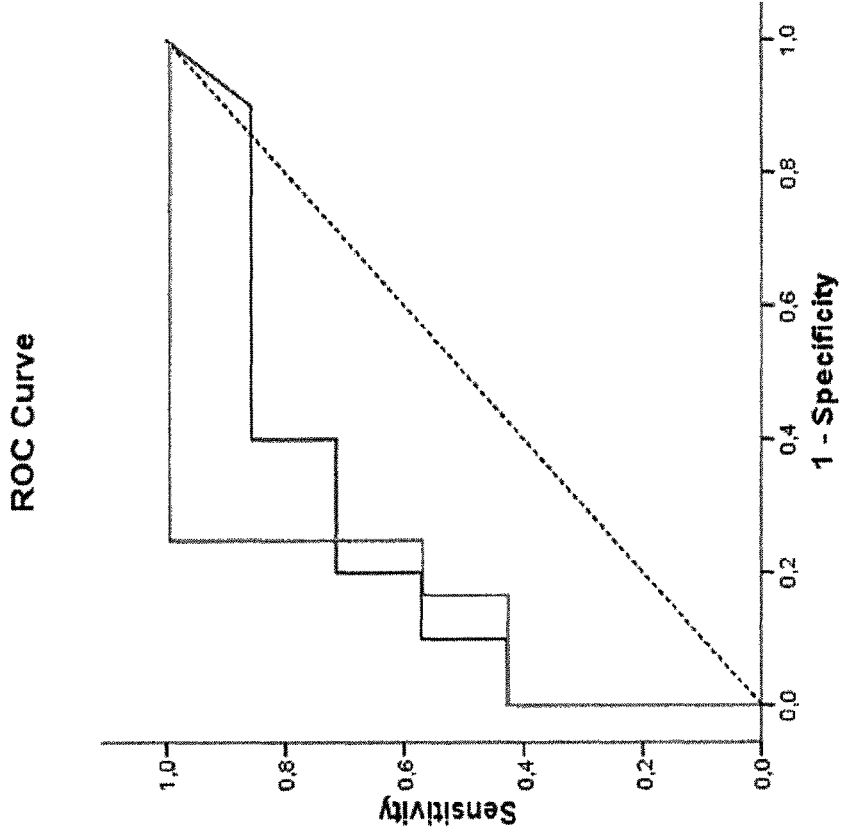

Figure 29:
ROC of initial FMLP induced expression of active ($A27_{fMLP}$) and IL-6 for the development of septic shock later during admission. FMLP induced expression of active FcγRII ($A27_{fMLP}$) proved to be a early, highly predictive marker for the development of septic shock, with an area under the curve of 0.869 ($p = 0.009$), superior to IL-6 (ROC 0.764, $p = 0.071$). The optimum expression cut off point with our settings was 2676 AU (25% of maximum values), as the sensitivity was 1.00 and the specificity 0.75. Red represents $A27_{fMLP}$ and blue represents IL-6.

Figure 30: Neutrophils were isolated from donors with septic shock and sorted for VLA4+ and VLA4- negative cells with a FACS/cell sorter (Facsvantage, Becton and Dickinson) via a method known to a person in the art. Hereafter, the cells were characterized in the context of binding to a ligand of VLA-4: VCAM-1. This was measured by determining the binding of neutrophils to VCAM-1 coated beads to neutrophils via a method essentially described for IgG coated beads by Bracke M, Dubois GR, Bolt K, Bruijnzeel PL, Vaerman JP, Lammers JW, Koenderman L. J Immunol. 1997 Aug 1;159(3):1459-65.

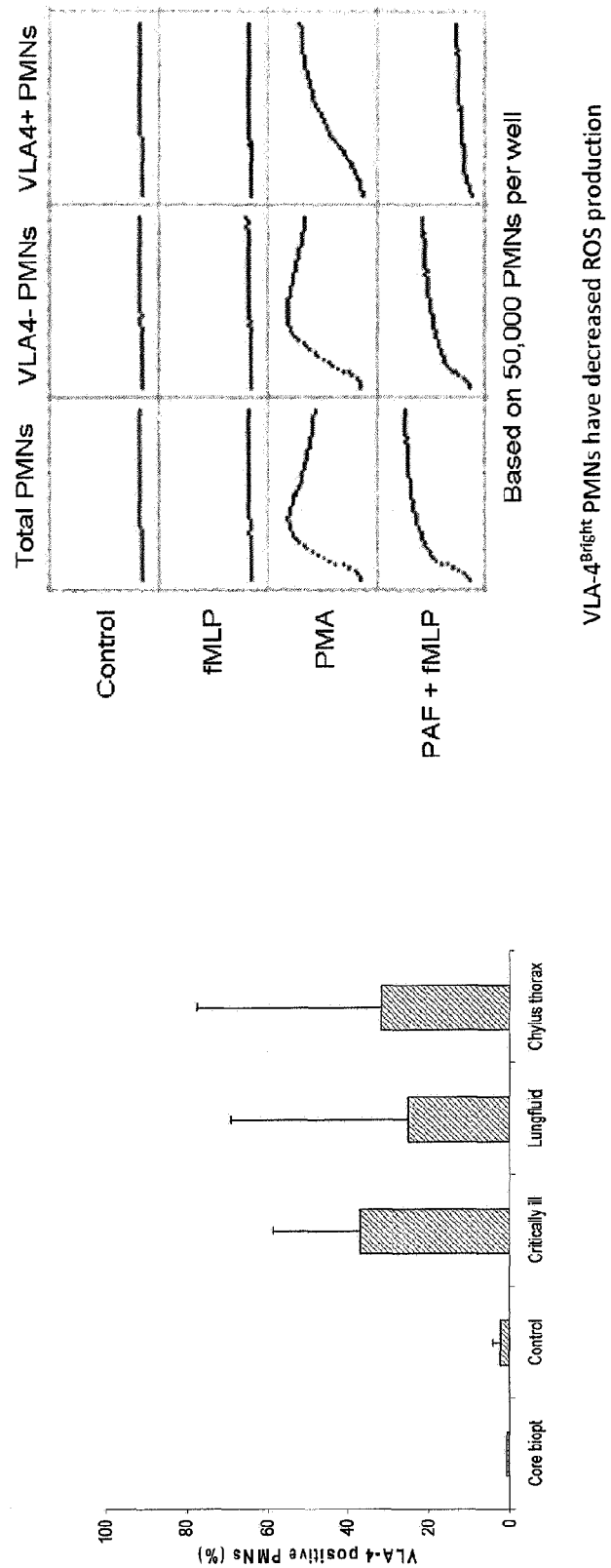

Figure 31: The amount of VLA-4 positive neutrophils are determined at different tissue locations by FACS analysis known to a person skilled in The art. VLA-4 positive cells were isolated by sorting via a flowcytometer and characterized in the context of activation of the respiratory burst. The method applied is described by Kuijpers et al (Kuijpers TW, van Bruggen R, Kamerbeek N, Tool AT, Hicsonmez G, Gurgey A, Karow A, Verhoeven AJ, Seeger K, Sanal O, Niemeyer C, Roos D. Blood. 2007 Apr 15;109(8):3529-37) which measures H2O2 induced reduction of AMPLEX red in a fluorimeter as a read out for activation of the respiratory burst.

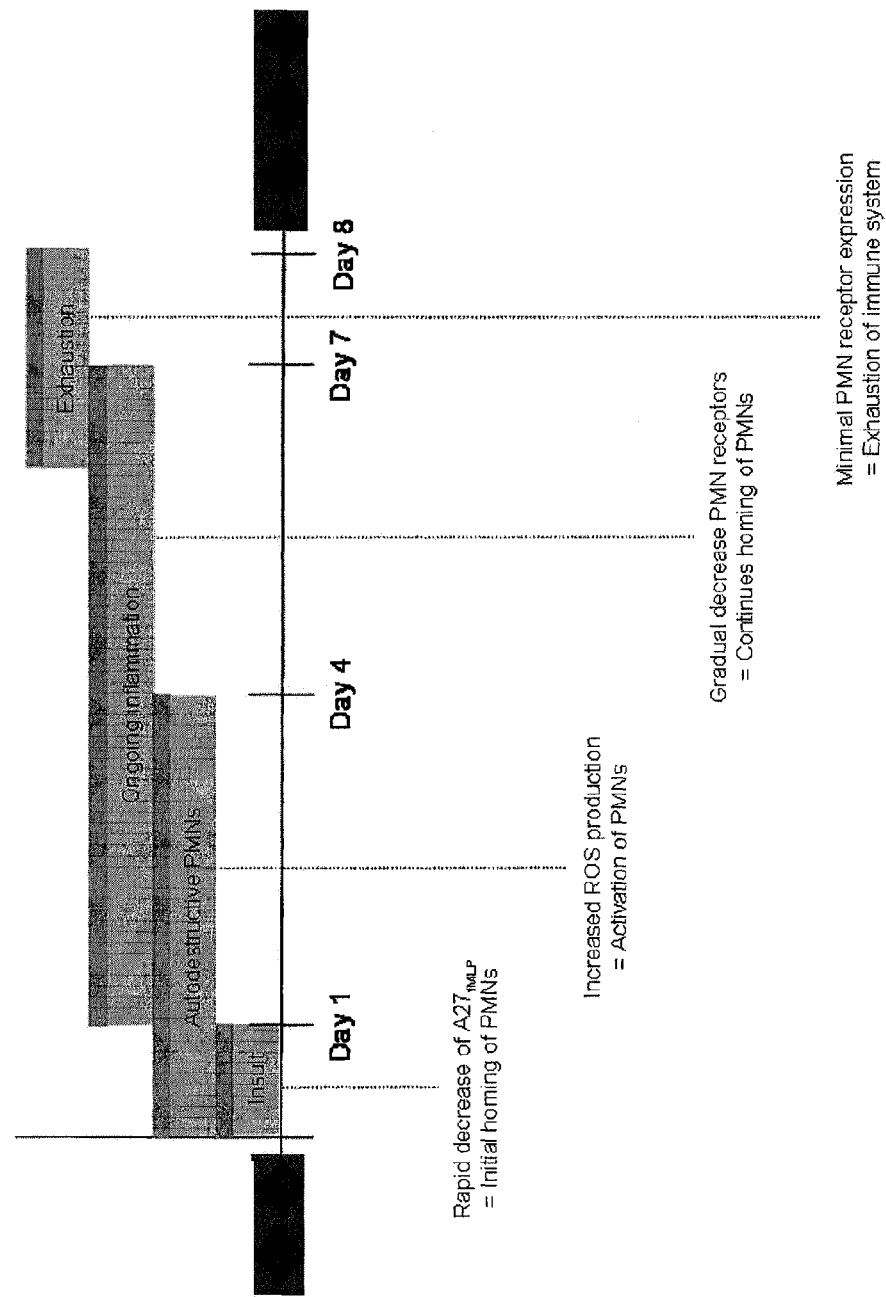
Figure 32: Model for the development of late septic shock after trauma: exhaustion of the innate immune reponse is the major risk factor

ACTIVATION EPITOPE OF FCγRII (CD32), BINDING MOLECULES THAT SPECIFICALLY BIND THE EPITOPE AND MEANS AND METHODS FOR THE DETECTION OF THE EPITOPE, AND USES OF SAID EPITOPE OR SAID BINDING MOLECULES

CROSS-REFERENCE TO RELATED APPLICATIONS

This application is the national phase of PCT application PCT/NL2007/050699 having an international filing date of 21 Dec. 2007, which claims benefit of European application No. 06077299.3 filed 21 Dec. 2006. The contents of the above patent applications are incorporated by reference herein in their entirety.

The invention relates to the field of immunology. The invention in particular relates to the detection of inflammatory cells. The invention further relates to an activation epitope of FcγRII (CD32), binding molecules that specifically bind said epitope, means and methods for the detection of the epitope, and uses of said epitope or said binding molecules.

Immunoglobulins and their Fc-receptors provide an important interface between innate and adaptive immunity (review Van de Winkel J G and Anderson. 1991. Biology of human immunoglobulin G Fc receptors. J Leukoc Biol. 1991 May; 49(5):511-24). Most studies on functional relationships between ligand and receptor have been performed with stably transfected cell lines such as IIA1-6 (Van Den Herik-Oudijk I E, Westerdaal N A, Henriquez N V, Cap el PJ, Van De Winkel J G. Functional analysis of human Fc gamma RII (CD32) isoforms expressed in B lymphocytes. J Immunol. 1994; 152: 574-85; and Budde P, Bewarder N, Weinrich V, Frey J. Biological functions of human Fc gamma RIIa/Fc gamma RIIc in B cells. Eur J Cell Biol. 1994; 64:45-60. These studies are complicated by the fact that the expressed FcR's on these cell lines have a functional phenotype in the absence of a co-stimulus. However, these cell lines do not necessarily contain all the control mechanisms by which normal innate immune cells can regulate the functionality of their receptors, a concept generally referred to as inside-out control. This paradigm has been particularly developed for control of function of integrin receptors (bv hynes 2002 Integrins: bidirectional, allosteric signaling machines. Cell. 2002 Sep. 20; 110(6): 673-87.). These studies show that the mere presence of integrin receptors is not sufficient for binding to their ligands. The cells need adhesion, chemokine, cytokine and/or growth factor induced signals in order to switch the conformational change the receptors from a non-functional towards a fully functional state (Kinashi T. Intracellular signalling controlling integrin activation in lymphocytes. Nat Rev Immunol. 2005; 5: 546-59). This can occur via at least a two-step mechanism through an intermediate functionality state (Ajroud K, Sugimori T, Goldmann W H, Fathallah D M, Xiong J P, Arnaout M A. Binding Affinity of Metal Ions to the CD11b A-domain Is Regulated by Integrin Activation and Ligands. J Biol Chem. 2004; 279:25483-8. Jones S L, Wang J, Turck C W, Brown E J. A role for the actin-bundling protein L-plastin in the regulation of leukocyte integrin function. Proc Natl Acad Sci USA. 1998; 95:9331-6). Full functionality of integrins is reached by inducing both a high affinity by a conformational change as well as an increased valency by clustering of the receptors.

We have shown that FcR's on human innate immune cells are also controlled by inside-out signals. Both FcγRII (CD32; Koenderman L, Hermans S W, Capel P J, van de Winkel J G. Granulocyte-macrophage colony-stimulating factor induces sequential activation and deactivation of binding via a low-affinity IgG Fc receptor, hFc gamma RII, on human eosinophils. Blood. 1993; 81: 2413-9.) and FcαRI (CD89; Bracke M, Coffer P J, Lammers J W, Koenderman L. Analysis of signal transduction pathways regulating cytokine-mediated Fc receptor activation on human eosinophils. J Immunol. 1998; 161: 6768-74.) endogenously expressed on granulocytes or exogenously expressed on stably transfected Ba/F3 cells are controlled by inside-out signals induced by cytokines. The increase in functionality of FcαRI and FcγRII is mediated by PI-3 kinase and p38 MAP-kinase pathways respectively (Bracke M, Coffer P J, Lammers J W, Koenderman L. Analysis of signal transduction pathways regulating cytokine-mediated Fc receptor activation on human eosinophils. J Immunol. 1998; 161: 6768-74; Bracke M, Nijhuis E, Lammers J W, Coffer P J, Koenderman L. A critical role for PI 3-kinase in cytokine-induced Fcalpha-receptor activation. Blood. 2000; 95: 2037-43.).

The molecular mechanisms have been partly elucidated for FcαRI (CD89) and point at a unique mode of control. On resting eosinophils as well as cytokine starved Ba/F3 cells stably transfected with FcαRI (CD89) the functionality of the receptor is actively suppressed by constitutive phosphorylation of an intracellular serine residue (Ser 263; Bracke M, Lammers J W, Coffer P J, Koenderman L. Cytokine-induced inside-out activation of FcalphaR (CD89) is mediated by a single serine residue (S263) in the intracellular domain of the receptor. Blood. 2001; 97: 3478-83).

Activation of the cells by cytokines leads to activation of the receptor by means of dephosphorylation of this serine residue. Many cell lines do not express this control module and as a consequence express their transfected FcR's in a default active form.

Initial experiments have shown that changes in functionality of FcR's on human eosinophils are modulated in the peripheral blood of patients with chronic asthma. These findings are consistent with the hypothesis that untouched innate immune cells express both integrins and FcR's in a low functionality state, which prevents artificial adhesion and/or activation of cytotoxicity under conditions of normal immune homeostasis. As soon as these cells interact with inflammatory mediators near or at the site of inflammation the cells are converted to a so-called primed state associated with the upregulated function of both integrins and FcR's (Bracke M, van de Graaf E, Lammers J W, Coffer P J, Koenderman L. In vivo priming of FcalphaR functioning on eosinophils of allergic asthmatics. J Leukoc Biol. 2000; 68: 655-61)).

BRIEF DESCRIPTION OF THE DRAWINGS

FIG. 1 shows methodology to measure the activation epitope present on FcγRII (CD32) on phagocytes recognized by the monoclonal phage antibodies CBS101481 (A17) and CBS101482 (A27).

FIG. 2 shows activation of neutrophils with inflammatory mediators induces a marked induction of expression of the activation epitope on FcγRII (recognized by CBS101481/A17) without inducing enhancement of expression of the receptor per se.

FIG. 3 shows patients with allergic asthma show activation of peripheral eosinophils characterized by an increase in expression of the activation epitope on FcγRII (recognized by CBS101481 and CBS101482) on peripheral blood eosinophils.

FIG. 4 shows the severity of allergic asthma (measured by bronchial hyperresponsiveness (AHR) and exhaled NO (eNO); methods known in the art) in patients with stable disease positively correlates with the activation of peripheral eosinophils characterized by enhanced expression of the activation epitope on FcγRII (recognized by CBS101481/A17 and CBS101482/A27) on peripheral blood eosinophils.

FIG. 5 shows individuals who actively smoke and patients with COPD show activation of peripheral monocytes characterized by increase in expression of the activation epitope on FcγRII (recognized by CBS101481/A17 and CBS101482/A27) on peripheral blood monocytes.

FIG. 6 shows the severity of COPD (measured by Fev1 a method inown in the art) in patients with stable disease positively correlates with the activation of peripheral monocytes characterized by enhanced expression of the activation epitope on FcγRII (recognized by CBS101481/A17 and CBS101482/A27) on peripheral blood monocytes.

FIG. 7 shows disease severity in children with cystic fibrosis correlates with activation of peripheral neutrophils characterized by an increase in expression of the activation epitope on FcγRII (recognized by CBS101481/A17 and CBS101482/A27) on peripheral blood neutrophils.

FIG. 8 shows disease severity in infants with RSV-induced lower respiratory tract disease as indicated by the fact that children needed standard clinical care (RSV-SC/moderate disease) or intensive care (RSV-IC/severe disease) relates to peripheral activation of eosinophils characterized by an increase in expression of the activation epitope on FcγRII (recognized by CBS101481/A17 and CBS101482/A27) on peripheral blood eosinophils.

FIG. 9 shows monoclonal phage antibodies CBS101481/A17 and CBS101482/A27 specifically recognize an activation epitope present on FcγRII (CD32).

FIG. 10 shows identification of neutrophil phenotypes: CD62L high/CD16 dim: young cells; CD62L high/CD16 high: normal cells; CD62L dim/CD16 high: old cells.

FIG. 11 shows identification of functional neutrophil phenotypes 2: increased expression of active FcγRII on hypersegmented cells.

FIG. 12 shows old cells are most sensitive for LPS-induced signals in vivo.

FIG. 13 shows identification of functional neutrophil phenotypes 3: the ratio of activated over non-activated expression of A17/A27 identifies refractoriness in hypersegmented cells.

FIG. 14 shows identification of functional neutrophil phenotypes 1: hypersegmented cells have upregulated cytotoxic potential.

FIG. 15 shows identification of functional neutrophil phenotypes 1: hypersegmented cells have suppressed chemotactic potential for C5a.

FIG. 16 shows LPS challenge in normal volunteers leads to differences in expression epitopes on FcgammaRII: biphasic response of A27 visualizes late occurrence of tissue derived cells in the peripheral blood.

FIG. 17 shows LPS challenge induced transient increase in responsiveness of blood neutrophils is followed by refractoriness.

FIG. 18 shows exhaustion of the innate immune system by trauma and sepsis I: presence of PMNs in lung, spleen and lymph nodes when bone marrow is depleted.

FIG. 19 shows identification of functional neutrophil phenotypes 1: hypersegmented cells have upregulated suppressive function on T-cell activation.

FIG. 20 shows tissue neutrophils are characterized by unique profile: $A17^{DIM}$, $A27^{HIGH}$ and $CD11b^{BRIGHT}$.

FIG. 21 shows kinetics of expression of priming epitopes on eosinophils in peripheral blood in response to allergen challenge in patients with asthma.

FIG. 22 shows priming of eosinophils, neutrophils and monocytes in mild stable asthmatics (phenotype 1), difficult-to-treat asthmatics (phenotype 2) and controls measured via cellular expression of αm (CD11b) and epitopes recognized by MoPhabs A17 and A27.

FIG. 23 shows resolution of disease after clinical treatment of an exacerbation of COPD is correlated with decrease in expression of the activation epitope on FcγRII (recognized by CBS101481/A17 and CBS101482/A27) on peripheral blood neutrophils.

FIG. 24 shows disease severity in patients with multi-trauma as indicated by the sepsis score (known to the art) is correlated with an increase in expression of the activation epitope on FcγRII (recognized by CBS101481/A17 and CBS101482/A27) on peripheral blood neutrophils.

FIG. 25 shows disease severity in patients with multi-trauma as indicated by the sepsis score (known to the art) is correlated with a marked decrease in the maximal expression of the activation epitope on FcγRII (recognized by CBS101481/A17 and CBS101482/A27) on neutrophils can be induced on peripheral blood neutrophils after activation of the blood with the innate immune stimulus fMLP (5 min 1 µM at 37 C).

FIG. 26 shows the relation between CD11b and $A27_{fMLP}$ with injury severity. FIG. 27 shows the relation between inflammatory score and pulmonary complications. FIG. 28 shows low activatibility of FcγRII (A27fMLP) on neutrophils within 12 hours after trauma predicts occurrence of septic shock.

FIG. 29 shows lack of fMLP-induced FcγRII predicts occurrence of septic shock.

FIG. 30 shows VLA-4$^{Bright}$ granulocytes after sorting are functionally binding
VCAM-1.

FIG. 31 shows exhaustion of the innate immune system by trauma and sepsis I: presence of functional end state VLA-4$^{Bright}$ PMNs in different body compartments and decreased cytotoxic function of VLA4+PMNs.

FIG. 32 shows a model for the development of late septic shock after trauma: exhaustion of the innate immune response is the major risk factor.

In the present invention a novel epitope on FcγRII (CD32) has been found. The appearance of the epitope on FcγRII (CD32) positive cells is associated with an enhanced activation state of FcγRII (CD32) positive cells of the innate immune system. The epitope is not present on cells FcγRII (CD32) positive immune cells that are not activated. Said FcγRII (CD32) epitope is therefore also referred to as a FcγRII (CD32) activation epitope. Without being bound by theory it is thought that FcγRII (CD32) is activated on innate immune rendering them responsive to further inflammatory signals. Innate immune cells expressing these FcR's in a functional state are often referred to as 'primed' innate immune cells. Similarly, this cytokine-induced pre-activation of innate immune cells is referred to as priming. Priming is required for full activation of the innate immune cells but is in itself not sufficient for the full activation. Additional signals are required for enabling full activation of the innate immune cells. There is consensus in the art that cytokine-induced pre-activation of innate immune cells is an integral part of the mechanisms leading to a controlled (i) homing of leukocytes to the tissues and (ii) activation of these cells in the tissues. Priming of granulocyte responses in the peripheral blood are typically found in the context of adhesion, whereas priming of cytotoxicity is mainly found in the tissues. These findings fit with the hypothesis that innate immune cells are controlled by multiple priming steps. Naive granulocytes (i.e. cells that have not interacted with inflammatory signals) from the bone-marrow express innate immune effector receptors (e.g. adhesion molecules, FcR's and complement receptors) in a low functional state. Untouched granulocytes exemplified by eosinophils are poorly responsive toward chemoattractants in the context of chemotaxis (Warring a R A, Koenderman L, Kok P T, Kreukniet J, Bruijnzeel P L. Modulation and induction of eosinophil chemotaxis by granulocyte-macrophage colony-stimulating factor and interleukin-3. Blood. 1991; 77: 2694-700), transendothelial movement (Moser R, Fehr J, Olgiati L, Bruijnzeel P L. Migration of primed human eosinophils across cytokine-activated endothelial cell monolayers. Blood. 1992 Jun. 1; 79(11):2937-45.) and other responses relying on a high affinity of integrins such as interaction with opsonized particles (Blom M, Tool A T, Kok P T, Koenderman L, Roos D, Verhoeven A J. Granulocyte-macrophage colony-stimulating factor, interleukin-3 (IL-3), and IL-5 greatly enhance the interaction of human eosinophils with opsonized particles by changing the affinity of complement receptor type 3.

Blood. 1994 May 15; 83(10):2978-84. Interaction of innate immune cells with inflammatory stimuli dramatically changes the phenotype of immune cells from a refractory to an activation prone phenotype. This process is herein referred to as "priming". Priming is defined in the context of specific responses. Priming of adhesion can be measured by a leftward shift of the dose response curve of platelet activating factor (PAF) induced chemotaxis (Warring a R A, Koenderman L, Kok P T, Kreukniet J, Bruijnzeel P L. Modulation and induction of eosinophil chemotaxis by granulocyte-macrophage colony-stimulating factor and interleukin-3. Blood. 1991 Jun. 15; 77(12):2694-700; Warring a R A, Mengelers H J, Kuijper P H, Raaijmakers J A, Bruijnzeel P L, Koenderman L. In vivo priming of platelet-activating factor-induced eosinophil chemotaxis in allergic asthmatic individuals. Blood. 1992 Apr. 1; 79(7): 1836-41). Priming of cytotoxicity can be quantified by the ratio between fMLP- or opsonized particles-induced responses in the presence and absence of platelet-activating factor or cytokines (Koenderman L, Yazdanbakhsh M, Roos D, Verhoeven A J. Dual mechanisms in priming of the chemoattractant-induced respiratory burst in human granulocytes. A Ca2+-dependent and a Ca2+-independent route. J Immunol. 1989 Jan. 15; 142(2):623-8; Koenderman L, Tool A T, Roos D, Verhoeven A J. Priming of the respiratory burst in human eosinophils is accompanied by changes in signal transduction. J Immunol. 1990 Dec. 1; 145(11):3883-8.). Priming of both adhesion and cytotoxicity is associated with enhanced expression of the priming epitopes recognized by A17 and A27.

The presence of the epitope on activated FcγRII/CD32 in a sample of circulating immune cells of an individual, in particular cells of the innate immune system is indicative for the presence of an active inflammation site in at least one of the organs of said individual. The epitope can be specifically detected using a binding molecule that specifically detects the epitope. The present invention therefore provides a method for selecting a FcγRII (CD32) specific binding molecule from a collection of binding molecules comprising contacting said collection of binding molecules with a FcγRII (CD32) molecule that expresses and/or displays an activation epitope and selecting from said collection a binding molecule that is specific for said activation epitope on said FcγRII (CD32) molecule. Examples of such specific binding molecules are the phage antibodies A17 and A27. These phage antibodies can be obtained from bacterial E. coli strains deposited under CBS120667 (A17) and CBS120668 (A27). The strains are deposited under the Budapest Treaty on the international recognition of the deposit of microorganisms for the purpose of patent procedure. Enclosed herein are copies of the BP/4 and BP/9 forms (FIGS. 33 and 34).

Said specific binding molecules can be selected from said collection using the specific binding characteristics of the mentioned phage antibodies. In a preferred embodiment said binding molecule is selected from said collection by selecting a FcγRII (CD32) specific binding molecule that is blocked from binding to FcγRII (CD32) by said phage antibody A17 and/or A27. The specificity for said activation epitope is preferably determined by detecting blocking of the FcγRII (CD32) specific binding of said FcγRII (CD32) specific binding molecule upon pre-incubation of said FcγRII (CD32) molecule with phage antibody A17 and/or A27. In another preferred embodiment said binding molecule is selected from said collection by selecting a FcγRII (CD32) specific binding molecule on the basis that the binding molecule mimics the specific binding of phage antibody A17 and/or A27 to said activation epitope on FcγRII (CD32). Thus the specificity for said activation epitope is preferably determined by determining that said FcγRII (CD32) specific binding molecule binds to a FcγRII (CD32) molecule expressing said activation epitope and does not bind to a FcγRII (CD32) molecule that does not express said activation epitope. The activation epitope of the present invention is a FcγRII (CD32) epitope that is specifically recognized by phage antibody A17 and/or A27. Many different types of specific binding molecules are presently known in the art. In a preferred embodiment said binding molecule is an antibody or a functional part, derivative and/or analogue thereof. Said antibody is preferably a monoclonal antibody or a functional part, derivative and/or analogue thereof. Preferably said binding molecule and/or antibody is not associated with a phage or a part of a phage. Preferably, said binding molecule and/or antibody is not a phage antibody.

In a further aspect the invention provides a binding molecule specific for a FcγRII (CD32) activation epitope of the invention. Such a binding specific binding molecule is obtainable by a method of the invention. In a preferred embodiment said binding molecule is a monoclonal antibody or a functional part, derivative and/or analogue thereof. A functional part, derivative and/or analogue comprises the same specific binding characteristics in kind, not necessarily in amount as an antibody of the invention. Preferred examples of a functional part of a monoclonal antibody are FAB-fragments, so-called heavy chain antibodies, VHH antibodies. In some antibody isotypes of camelids from the old world (camels, dromedaries) or from the new world (llamas, vicugna) the light-chain is missing. Furthermore, their heavy-chain is devoid of the CH1 domain due to an unconventional splicing event during the mRNA maturation. The antigen binding fragment of the heavy-chain antibodies is therefore comprised in one single domain, the unique N-terminal variable domain referred to as VHH that replaces a four-domain Fab fragment in the Ig structure. Such camelid single heavy chain antibodies are functional in antigen/epitope recognition and are therefore preferred examples of a part of a monoclonal antibody of the invention. Particularly preferred parts of monoclonal antibodies are the unique N-terminal variable domains of the single heavy chain antibodies (VHH). Currently many different derivatives of antibodies are used. In the present invention a derivative of an antibody preferably comprises at least a constant region of an antibody. The variable regions and in particular the CDR regions may be obtained from another antibody thus producing a chimeric antibody, or be completely artificial (not occurring in nature). In a particularly preferred embodiment, the invention provides an antibody or a functional part, derivative and/or analogue thereof comprising at least one CDR region from phage antibody A17 and/or A27 described herein above. In another preferred embodiment at least one CDR region is artificial; preferably at least the CDR3 region is artificial. It is also possible to mimic antibodies by molecules that act in a similar fashion. For instance, many molecules have domains comprising so-called Ig folds that resemble the Ig fold of antibodies including the presence therein of similar CDR like regions and framework regions. A non-limiting example of such a molecule is fibronectin type. These domains are often referred to as monobodies or nanobodies. Such domains are preferred analogues of a part of an antibody of the invention.

To prevent any binding of an antibody or functional part, derivative and/or analogue of the invention to Fc receptor expressing cells it is preferred that the constant part of said antibody is modified and/or removed such that binding to Fc receptors is prevented.

In another preferred embodiment said specific FcγRII (CD32) binding molecule of the invention is a small molecular antagonist or modified FcγRII (CD32) ligand. Such small molecular antagonist or (modified) FcγRII (CD32) ligands are typically isolated from high throughput screens using an indicative assay. The phage antibodies A17 and A27 described herein above are associated with a phage. The phage is part is often undesired, for instance in clinical settings. In one embodiment the invention therefore provides an antibody or a functional part, derivative and/or analogue thereof comprising at least the CDR3, and preferably also the CDR 1 and CDR2 of phage antibody A17 and/or A27. Preferably, said antibody further comprises additional antibody parts of said phage antibodies. Preferably said binding molecule and/or antibody is not associated with a phage or a part of a phage. Preferably, said binding molecule and/or antibody is not a phage antibody.

In another aspect the invention provides a method for specifically detecting a FcγRII (CD32) molecule comprising contacting said FcγRII (CD32) molecule with a binding molecule according to the invention and detecting specific binding of said binding molecule. Also provided is a method for determining whether a FcγRII (CD32) expressing cell comprises a FcγRII (CD32) molecule that displays an activation epitope of the invention, comprising contacting said cell with a binding molecule according the invention and detecting specific binding of said binding molecule. The activation epitope can be detected on any FcγRII (CD32) expression cell. Cell lines provided with FcγRII (CD32) often express the activation epitope as inside out signalling is always active in these cells. Cell lines typically though not necessarily lack the specific enzyme activity that actively keeps the FcγRII (CD32) inactive in naturally FcγRII (CD32) expressing cells. In a preferred embodiment said cell is a hemopoietic cell. Cells of the myeloid lineage are preferred as these cells naturally express FcγRII (CD32). Preferably said cell is a phagocyte. Preferred phagocytes are granulocytes, monocytes/macrophages. Preferred granulocytes are neutrophils and eosinophils, a monocyte/macrophage. FcγRII (CD32) expressing myeloid precursors of the cells are also preferred cells.

The invention further provides a method for determining whether a cell containing sample comprises an activated phagocyte, said method comprising contacting said cells in said sample with a binding molecule according to the invention and determining whether said binding molecule specifically bound a cell in said sample. Preferably said sample comprises blood cells. In another preferred embodiment said sample comprises Broncho alveolar lavage (BAL) cells, cells from synovial fluid, liquor, peritoneal ascites, pleural fluid and/or lymph. As innate immune cells that have migrated from the bloodstream to the organs are activated it is also within the scope of the present invention to detect the activated FcγRII (CD32) epitope on such intra-organ cells. This is preferably done in a sample containing a biopsy of such an organ. It is further possible to determine the presence of the epitope in any other body fluid sample known to contain inflammatory cells.

Preferably said method further comprises detecting a phagocytes in said sample. This allows easy determination of the fraction of phagocytes that comprises FcγRII (CD32) exposing said activation epitope.

An important aspect of the present invention is the correlation of the number of innate immune cells in a fluid sample from an individual that express an activation epitope of the present invention and the degree of inflammation that said individual is experiencing. The present invention therefore further provides a method for determining whether a cell containing sample comprises an activated phagocyte, wherein said sample is a sample of an individual suffering from or at risk of suffering from an organ-bound inflammatory disease, septic shock, an allergy, an auto-immune disease, a graft-versus host disease or a host versus graft disease.

It is preferred that said individual is not suffering from or at risk of suffering from a lung disease or an allergy. It is preferred that said individual is not suffering from or at risk of suffering from COPD or allergic asthma.

As a binding molecule of the invention specifically binds FcγRII (CD32) expressing cells that express an activation epitope of the invention, it is possible to specifically target these cells. It is therefore also possible to target such cells for destruction, for instance and not-limited to, coupling said binding molecule to a killing agent and/or toxin. A non-limiting example of a killing agent and/or toxin that is currently used and/or prepared for use in humans is ricinB and/or cytotoxic radioactive probes. An interesting alternative is a chimeric protein comprising of the molecule that specifically binds FcγRII (CD32) expressing cells that express an activation epitope of the invention and an epitope that specifically activates cytotoxic cells of the immune system such as CD8+ T-cells, NK-cells, K-cells and/or NK-T-cells and LAK-cells. This treatment can use cytokines such as IL-2 as adjuvant for these immune cells. Removal of FcγRII (CD32) expressing cells that express an activation epitope of the invention results in a reduction of the inflammation and thereby ameliorates inflammation symptoms in the affected individual. The present invention therefore provides the use of a binding molecule according to the invention, for the preparation of a medicament for the treatment of an individual suffering from or at risk of suffering from an inflammation. Preferably, this strategy can be applied to acute inflammatory diseases, such as acute respiratory distress syndrome and inflammation caused by ischemia/reperfusion that have a high morbidity and mortality. Prophylactic administration of the binding molecule reduces the inflammation symptoms that otherwise would affect the individual. A mentioned herein above is said binding molecule preferably an antibody, preferably a monoclonal antibody or a functional part, derivative and/or analogue thereof. For use in human individuals it is preferred that the antibody is a human antibody, or humanized antibody. An antibody can be humanized in several ways, for instance and not limited to, grafting of artificial CDR regions onto a human antibody backbone and/or tailoring the antibody, for instance a murine antibody such that at least one typically human T-cell epitope therein is removed. Preferably all dominant human T-cell epitopes are removed, at least for the prevalent HLA molecules. In a preferred embodiment said individual is suffering from or at risk of suffering from an organ-bound inflammatory disease, septic shock, an allergy, an auto-immune disease, a graft-versus host disease or a host versus graft disease. Preferably said individual is not suffering from or at risk of suffering from COPD or allergic asthma. The invention further provides a binding molecule for determining in a sample obtained from an individual scheduled for or undergoing immune therapy, the efficacy of said therapy.

Also provided is a method for determining the degree of activation of an immune cell through FcγRII (CD32) comprising quantifying the binding of a binding molecule according to the invention on said immune cell. Preferably said cell is a cell is an immune cell of the innate immune system. Preferably said method further comprises quantifying the ratio of binding of an agent recognizing the activation epitope on FcγRII (CD32) and a pan FcγRII (CD32) specific antibody. Preferably, wherein comprising quantifying the binding of a binding molecule according to the invention on a collection of said immune cells and quantifying the binding of a pan FcγRII (CD32) specific antibody on a collection of said immune cells.

Also provided is a method for determining the degree of refractoriness of innate immune for innate immune stimuli. Peripheral blood immune cells obtained from patients with acute severe inflammation are refractory to activation with innate immune stimuli in the context of expression of the activation epitope on FcγRII (CD32) quantified by the binding of a binding molecule according to the invention on said immune cell. Preferably said cell is a cell is an immune cell of the innate immune system. Preferably said method further comprises quantifying the ratio of binding of an agent recognizing the activation epitope on FcγRII (CD32) in the presence and absence of an innate immune stimulus, preferably FMLP. Preferably, wherein said quantifying comprises the binding of a binding molecule according to the invention on a collection of said immune cells and quantifying the binding of a pan FcγRII (CD32) specific antibody on a collection of said immune cells.

Also provided is a method for determining the degree of activation of an immune cell through FcγRII (CD32) comprising quantifying the binding of a binding molecule according to the invention on said immune cell. Preferably said cell is a cell is an immune cell of the innate immune system. Preferably said method further comprises quantifying the ratio of binding of an agent recognizing the activation epitope on FcγRII (CD32) and a pan FcγRII (CD32) specific antibody. Preferably, comprising quantifying the binding of a binding molecule according to the invention on a collection of said immune cells and quantifying the binding of a pan FcγRII (CD32) specific antibody on a collection of said immune cells.

Further provided is a method for determining whether an individual is suffering from an inflammation comprising, determining in a sample containing cells from a bodily fluid containing or suspected of containing immune cells of said individual, the binding of a binding body according to the invention on said cells. Preferably for determining the course of an inflammatory disease in said individual. Preferably said method further comprises determining said binding in a similar sample of said individual taken at a different time point. Preferably said method further comprises providing said individual with anti-inflammatory treatment, preferably comprising providing said individual with an anti-inflammatory drug. Said method preferably further comprises determining the efficacy of said anti-inflammatory treatment.

The present invention also relates to a phagocyte-recognizing agent, preferably a FcγRII (CD32) specific binding molecule specific for an activation epitope expressed on functionally active FcγRII (CD32) that is recognized by at least one bacteriophage such as may be isolated from the strains having accession numbers CBS120667 and 120668. Such an agent, preferably a (monoclonal) antibody is useful for establishing the presence of an (organ bound) inflammation and the severity thereof. This is preferably done by determining and preferably quantifying the presence of an FcγRII (CD32) activation epitope on peripheral blood cells. In addition, the agent may be used for eliminating preactivated phagocytes from blood, for example, by using a carrier-bound agent which, after contact between carrier and blood, are separated from each other. In a further embodiment of the invention the agent is combined with a group deactivating or even killing the (preactivated) phagocyte. Here an antibody provided with a cell-killing unit, for example a RicineB-chain, or a bi-specific antibody provoking the immune-system to eliminate the preactivated phagocyte is a preferred example. The group is preferably (chemically) attached to the agent or is part thereof, for example because it has been prepared by genetic engineering. Both chemical coupling as well as genetic engineering are well-known techniques in the art.

The invention also relates to a pharmaceutical composition comprising a phagocyte-recognizing deactivating agent capable of recognizing the antigen that is recognized by at least one bacteriophage as can be isolated from the strains having accession numbers CBS 120667 and 120668 together with a pharmaceutically acceptable excipient or carrier. The invention also relates to a method of detecting a preactivated phagocyte, allowing the specific detection of a preactivated phagocyte. In one embodiment detection of binding of a FcγRII (CD32) specific binding molecule of the invention is achieved by fluorescently labelling said binding molecule and detecting of binding to the surface of the phagocyte by a fluorescence microscope or flowcytometer (FACS). The label may also be an enzyme, whereby for example the activity of the enzyme can be used in different methods known in the art.

The detection of phagocytes expressing the activation epitope on FcγRII (CD32) can be used for the determination and monitoring of severity and phenotype of the inflammation processes in patients with chronic inflammatory diseases (e.g. asthma, COPD, chronic inflammatory bowel diseases, chronic inflammatory liver diseases). It can further be used for determination and monitoring of severity and phenotype of the rejection reaction seen in patients after organ transplantation. It can also be used for determination and monitoring and severity of the processes that can initiate the pathological processes that lead to ARDS and multiple organ failure after multiple trauma, major surgery and acute inflammatory conditions as seen as e.g. pancreatitis. Said detection can also be used for monitoring of anti-inflammatory therapy for different chronic inflammatory diseases. It may further be used for monitoring of success of therapy utilizing monoclonal antibodies to target immune effector cells to diseased cells in the patient.

The present invention demonstrates that the activation epitope on FcγRII (CD32) is induced under several clinical conditions such as on eosinophils in allergic asthma (see FIGS. 4 and 5), on monocytes/granulocytes in COPD (see FIGS. 6, 8 and 9), on eosinophils in infants infected with respiratory syncytial virus (RSV) (see FIG. 7). Aberrant expression of the activation epitope of FcγRII (CD32) has also been found on phagocytes in patients with multitrauma at risk for development of ARDS and/or multi organ failure (see FIGS. 10 and 11). Determination of the expression of the activation epitopes of FcγRII (CD32) on leukocytes as read-out of treatment success in therapy of chronic inflammatory diseases is depicted in FIG. 9. Here the expression of activated FcγRII (CD32) on neutrophils normalizes during successful therapy of clinical exacerbations of COPD.

Patients suffering severe injury, such as trauma patients and patients undergoing major surgery, are at risk for severe inflammatory complications in two distinct phases; an early phase 1-4 days after injury and a late phase 8-14 days after injury. The most severe inflammatory complication is multiple organ failure, which can occur in two phases. Early multiple organ failure (MOF) is usually not associated with a preceding infection and is thought to be the result of an excessive inflammatory response (Severe Inflammatory Response Syndrome [SIRS]) in reaction to the sustained injuries. Late MOF is thought to be a consequence of sepsis or uncontrolled infection during a state of immune paralysis (Compensatory Anti-inflammatory Response Syndrome [CARS]). This hypothesized alteration of the patients' inflammatory status during two distinct clinical states is called the biphasic inflammatory response.

Analysis of soluble inflammatory markers (such as cytokines; e.g. IL-6 and IL-10) did not provide satisfactory results to accurately test the biphasic response hypothesis. The initial pro-inflammatory response has been qualitatively identified, nevertheless the quantification of its magnitude based on soluble markers remains difficult. Research on the development of sepsis during CARS has been less successful. Most studies covered the role of lymphocytes and monocytes in this process, but remained inconclusive. In the present invention it was found that PMNs (polymorphonuclear granulocytes or neutrophils) are partially dysfunctional directly after trauma. Spontaneous PMN functions are increased, whereas the maximal activation in response to bacterial products is decreased. It is not clear whether this phenotype occurs by direct down-regulation of neutrophil functionality, or by depletion of adequate functioning cells from the peripheral blood by homing to the tissues. Nevertheless, these changes in the circulation can, as shown in the present invention, be used to assess the inflammatory status of a patient. In addition, this early phenotype is associated with the clinical symptoms of early organ damage and late immune paralysis.

This present invention among others provides the identification of the biphasic inflammatory response after injury by determination of neutrophil phenotypes. In addition, it was found that excessive and early (within 24 hrs) pro-inflammatory response was related to the later development of immune dysfunction and septic shock and other complications common in subjects that have suffered trauma. Quantification of the pro-inflammatory response in trauma patients and comparison of this quantification to the types of complications observed in trauma patients revealed a striking correlation between the degree of the pro-inflammatory response and the complications that can be expected in these trauma patients. It was found that the level of a polymorphonuclear granulocyte (PMN) receptor on blood cells of the trauma patients is indicative for the degree of the pro-inflammatory response. This is particularly so for the FcγRII (CD32) receptor. The fact that the level of a PMN receptor varies in such blood cells can be due to the (dis)appearance of certain subtypes of blood cells from or in the circulation, the up- or downregulation of the specific PMN receptor on cells in the blood, it can be the result of a combination thereof or it can have a different reason. Whatever the reason, the level of such PMN receptor on blood cells was found to be indicative for the degree of the pro-inflammatory response. The invention thus further provides a method for estimating a risk of complications in an individual that has suffered a trauma comprising determining the level of at least one polymorphonuclear granulocyte (PMN) receptor epitope on blood cells of said individual wherein at least one of said receptors is FcγRII (CD32) receptor and estimating said risk from said level.

The estimation is more accurate when the level of at least two PMN receptors is determined on the blood cells. In a preferred embodiment said the level of the Mac-1 (CD11b) receptor is determined on said blood cells. The level determined for the FcγRII (CD32) receptor is very indicative for determining differences in the degree of the pro-inflammatory response in relation to a relatively mild to average injure severity. The level of CD11b is particularly indicative in relation to an average to extreme injure severity. Combined the receptors provide a strikingly accurate measure of the level of the pro-inflammatory response and the complications that can be expected in trauma patients. In a preferred embodiment, the level of FcγRII (CD32) receptor is given a number from one to five, based on the inverse of the level of the receptor detected on the blood cells. With the number one given for a high detected level and the number 5 given when low levels are detected. For CD11b the numbers 1 and 5 are assigned when respectively low levels and high levels are detected. The sum of the two numbers then gives an accurate measure for the pro-inflammation score. In this inflammatory score a lower number is indicative for a relatively low pro-inflammation response and a high number vice versa for a high pro-inflammation response. In the present invention it was found that particular pro-inflammation scores are associated with a risk for a certain type of complication in trauma patients. Preferred complications are a pulmonary complication or septic shock. Particularly preferred complications are cardiac failure, SIRS without pulmonary complications, pneumonia, and ALI/ARDS.

The blood cells are preferably collected from said individual within 24 hours after suffering said trauma. In this time period, the determined level and associated scores are particularly correlated with the type of complication the trauma patients is at risk of. Preferably, said blood cells are collected within 12 and more preferably within 6 hours of suffering said trauma.

Trauma can be subdivided into several types. Two main types are trauma as a result of a physical/mechanical intervention with the body and trauma as a result of a hyper-inflammation caused by an exacerbation of inflammatory disease, preferably a chronic inflammatory disease. Preferred causes of trauma for a method of the invention are a (motor) vehicle accident trauma, an assault trauma, a fall of height trauma, a penetration trauma, post-operative trauma, or an exacerbation of asthma, COPD, or allergy. Preferably said trauma is the result of a physical/mechanical intervention with the body.

In the present invention it was found that trauma induces rapid changes in the PMN cells in the blood. Without being bound by theory it is believed that upon suffering the trauma PMN are massively recruited from the blood and leave there from to enter the tissue. Simultaneously, at least some mature cells remain and/or enter the circulation from the tissues. As a result the ratio of young/immature/normal PMN and mature PMN changes very quickly upon suffering said trauma. It was found that particularly mature cells are indicative for the level of the pro-inflammatory response upon trauma. Thus in a preferred embodiment a method for estimating a risk of complication in an individual suffering from trauma further comprises determining maturity of said PMN. It was found that mature cells are not as responsive to immune stimuli of the innate immune system. Thus with increasing pro-inflammatory response, the level of activated FcγRII (CD32) receptor on PMN decreases. I.e the difference between the level on PMN in collected blood cells and an aliquot thereof that has in vitro been exposed to said stimulus decreases. Thus in a preferred embodiment of the invention said PMN receptor epitope is an activation epitope of said receptor. Said activation epitope is preferably an epitope specifically recognized by phage antibody A27. For determining the inflammation score it is preferred that the level of the activation epitope that is specifically recognized by phage antibody A27 is determined in blood cells of said individual that have been exposed in vitro, to a stimulus of the innate immune system. Preferably said stimulus is fMLP. In a method wherein said further receptor comprises CD11b, it is preferred that the level of said receptor is determined in blood cells that have not in vitro been exposed to a stimulus of the innate immune system. Preferred blood cells for measuring the level of a PMN receptor are phagocytes. Preferably said cells are granulocytes. More preferably said cells are neutrophils.

The invention further provides a method for determining a treatment of an individual suffering from a chronic inflammation said method comprising contacting a sample containing blood cells of said individual with a binding molecule specific for an activation epitope on FcγRII (CD32), determining whether said sample comprises eosinophils or neutrophils that have specifically bound said binding molecule and determining said treatment. It has been found that chronic inflammation can be subdivided into at least two groups based on whether chronic inflammation is associated with the presence of an activation epitope on FcγRII (CD32) on eosinophils, neutrophils or both. It has been found that patients suffering from chronic inflammation with eosinophils comprising said activation epitope are often responsive to anti-inflammatory medication, whereas patients where the activation epitope is predominantly present on neutrophils are often unresponsive to said medication. Patients having significant levels of said activation epitope on both eosinophils and neutrophils often respond to said medication in so far as the eosinophils part is involved. Individuals suffering from chronic inflammation that receive anti-inflammation medication therapy can be tested for compliance with said therapy by analysing an activation epitope on FcγRII (CD32) on eosinophils and/or neutrophils. Medication of individuals having a pre-medication status involving the presence of said activation epitope on eosinophils, results in a decrease in the level of said activation epitope on eosinophils. The amount of reduction corresponds to the success and/or compliance with the anti-inflammation medication therapy. Thus the invention further provides a method for determining treatment success and/or compliance with treatment in an individual suffering from a chronic inflammation, said method comprising a sample containing blood cells of said individual with a binding molecule specific a PMN receptor, determining the level of binding of said binding molecule and determining from said level whether treatment of said individual is successful and/or whether said individual complies with treatment. Preferably said binding molecule is specific for an activation epitope on FcγRII (CD32). Preferably said binding molecule is specific for the activation epitope specifically recognized by phage antibody A27. Said anti-inflammatory medication preferably comprises glucocorticosteroid medication.

Various types of chronic inflammation exist and are preferred in the present invention (asthma, chronic obstructive pulmonary disease (COPD), chronic rejection reactions after transplantation, inflammatory bowel disease, multiple sclerosis, eczema, psoriasis, allergy, chronic liver failure, rheumatoid arthritis, brochiolitis obliterans syndrome, interstitial lung diseases, systemic lupus erythomatosus, fibrotic disease and atherosclerosis, chronic infection/colonization with bacteria and/or parasites and/or viruses and glomerulo nephritis). In a preferred embodiment said chronic inflammation comprises asthma, COPD, allergy, and chronic rejection. In a preferred embodiment said chronic inflammation comprises asthma. In a preferred embodiment the invention provides a method for determining an asthma type of an individual suffering from asthma comprising detecting in a sample comprising blood cells of said individual an activation epitope of FcγRII (CD32) on eosinophils or neutrophils. Preferably said method further comprises typing said asthma as an asthma that is responsive to anti-inflammatory medication, preferably glucocorticosteroid medication when eosinophils displaying said activation epitope are detected. In the present invention it is said that an individual at least comprises eosinophils and/or neutrophils respectively displaying said activation epitope when the level detected is more than 1 standard deviation higher than the level detected in a healthy individual. Preferably, said level is more than 2 standard deviations higher. Preferably said method further comprises typing said asthma as an asthma that is refractory to anti-inflammatory medication, preferably glucocorticosteroid medication when neutrophils displaying said activation epitope are detected.

There are various PMN receptors that can be used in the present invention. Preferred PMN receptors are CD11b, CD16, CD32, CD62L, CD88, CD181, CD182, FcγRII (CD32) or VLA-4 (CD49d). Thus in a preferred embodiment said binding molecule is specific for CD11b, CD16, CD32, CD62L, CD88, CD181, CD182, FcγRII (CD32) or VLA-4 (CD49d). Preferred FcγRII (CD32) binding molecules are binding molecules specific for the activation epitope on FcγRII (CD32) that is recognized by phage antibody A17 and/or A27. Preferably said FcγRII (CD32) binding molecule is specific for the activation epitope on FcγRII (CD32) that is recognized by phage antibody A27. It has been found that the level of PMN receptors on blood cells in chronic inflammation patients is particularly indicative for treatment success, compliance with therapy when neutrophils are scrutinized. Thus preferably said the level of binding of said binding molecule is determined on neutrophils in said sample. Preferably said blood cells have, upon collection of said individual, been activated with an activator of innate immune cells, preferably of PMN. Preferably said method further comprises comparing said level of binding before and after said activation. It has been found that the response to said activator is indicative for the state of the disease. For instance, the appearance or increase of VLA-4 (CD49d) receptor positive PMN in the circulating blood indicates that the innate immune response is as good as exhausted. Very often this indicates that said patient has only a short time to live. The correlation between the appearance or increase of VLA-4 positive PMN in the blood and exhaustion/expected death of the individual is good also without determining the level of an activation epitope on FcγRII (CD32) that is recognized by phage antibody A17 and/or A27 on said cells In a further aspect of the invention it was found that mature granulocytes have properties in common with regulator T-cells. Addition of mature granulocytes to a system of T-cells decreases the response of the T-cells to a T-cell stimulus. Without being bound by theory it is believed that mature granulocytes entering the blood are derived from tissues and migrate via the blood to antigen specific immune centres such as lymph nodes. Upon arrival these granulocytes dampen the antigen specific immune response to counteract and/or prevent over-stimulation thereof. The immune response dampening effect of these cells is particularly present when they are derived from an individual that is recovering from a strong stimulus of the innate immune response. The mature cells can be identified by their morphology as cells having a highly segmented nucleus. Other identification methods include the presence or absence of specific markers. In a preferred embodiment said cells are identified and/or collected on the basis of their appearance as CD62L dim en CD16 bright. On the other hand, it was found that addition of young granulocytes to a system of T-cells enhances the effect of an immune stimulus provided to these T-cells. Also these cells are preferably collected from an individual that is recovering from a strong stimulus of the innate immune response. Without being bound by theory it is thought that these young cells are destined to enter tissue and there deliver their stimulatory function. Thus the present invention further provides a method for modulating the effect of an immune stimulus in a system comprising T-cells, comprising adding a sample of granulocytes to said system. Preferably said immune response is an antigen specific immune response. Preferably said modulation comprises dampening said effect by adding a sample of mature granulocytes. Said mature granulocytes are among others characterised by being more refractory to (further) activation when compared to $CD16^{Bright}$, $CD62L^{Bright}$ granulocytes. Said (further) activation is among others detectable through detecting the presence of an activation epitope on FcγRII (CD32). Preferably, the detected activation epitope is an epitope specifically detected by the phage antibody A27. The sample of granulocytes is preferably depleted for banded granulocytes. Such cells reduce the dampening effect of the mature granulocytes.

In a preferred embodiment the invention provides a method for enhancing the effect of a stimulus for T-cells in a system comprising T-cells by adding a sample of banded granulocytes to said system. Said young cells are among others characterised by a banded nucleus and are therefore also referred to in the art as banded cells. A further method for characterising and/or collecting these cells is on the basis of the presence of specific markers. Preferred markers are CD16 and CD62L. In a preferred embodiment said cells are characterised/collected on the basis of being $CD16^{dim}$ and $CD62L^{bright}$. Said cells are further characterised in that these granulocytes are more responsive to (further) activation when compared to $CD16^{Bright}$, $CD62L^{Bright}$ granulocytes.

In a preferred method for modulating the effect of an immune stimulus said granulocytes display a granulocyte (pre)activation marker, preferably an activation epitope of FcγRII (CD32). Preferably the epitope recognized by the phage antibody A27. The above mentioned mature and young granulocytes can not only be used to modulate the effect of an immune stimulus for T-cells. They can also be used to modulate an existing T-cell mediated immune response, i.e. suppress activated T-cells or activate resting T-cells respectively in case of mature and young granulocytes as defined herein above. The cells can similarly be used to modulate an inflammatory response, the inflammatory response being down modulated in case of mature granulocytes and upregulated in case of young granulocytes. The above mentioned mature granulocytes can also be obtained in vitro by maturing granulocytes in vitro, either derived from the blood of an individual or derived from cultures containing hemopoietic progenitor and/or stem cells, or from cultures stemming from omnipotent stem cells such as derived from an embryo, cultured embryonal stem cells and the like. The above mentioned young granulocytes can also be obtained in vitro by stimulating granulocyte formation in vitro, either derived from the blood of an individual or derived from cultures containing hemopoietic progenitor and/or stem cells, or from cultures stemming from omnipotent stem cells such as derived from an embryo, cultured embryonal stem cells and the like.

To reduce a counteraction of the modulation by other cells it is preferred that said sample is enriched for said granulocytes. In a preferred embodiment said mature cells and/or said young cells are neutrophils.

The invention further provides a method for typing granulocytes said method characterised in that said granulocytes are characterised as suppressor granulocytes. Such suppressor granulocytes are preferably the herein above described mature granulocytes. The invention further provides the use of mature granulocytes for their regulator T-cell properties.

The invention further provides the use of a binding molecule of the invention specific for an activation epitope on FcγRII (CD32), for the preparation of a medicament enriched for suppressor neutrophils for the treatment of an individual suffering from or at risk of suffering from an inflammation, preferably a chronic inflammation. Preferably said individual is suffering from or at risk of suffering from an organ-bound inflammatory disease, septic shock, an allergy, an auto-immune disease, a graft-versus host disease or a host versus graft disease.

The invention further provides the use of a binding molecule of the invention specific for an activation epitope on FcγRII (CD32), for the preparation of a medicament comprising neutrophils devoid of suppressor neutrophils to boost immunotherapy of an individual suffering from or at risk of suffering from cancer. Preferably said granulocytes are active young bone marrow derived granulocytes ($CD62L^{BRIGHT}$ and $CD16^{DIM}$). Preferably said granulocytes are activated granulocytes characterized by the expression of active FcγRII (cD32). Preferably said sample is enriched for young bone marrow derived activated granulocytes characterized by the expression of active FcγRII (CD32).

The invention further provides a method for typing granulocytes said method characterised in that said granulocytes are characterised as young active bone marrow derived granulocytes.

A sample of blood cells can be any type of sample. It is preferred that said sample is a whole blood sample. When cells purified in some way from whole blood are used it is preferred that IgG3 is present when detecting an activation epitope of FcγRII (CD32). It has been found that the presence of IgG3 enhances the binding/detection of a binding molecule specific for said activation epitope. The invention thus further provides a collection of granulocytes that has been provided with an IgG3 antibody, preferably from another source then whole blood.

The invention further provides the use of a binding molecule specific for an activation epitope on FcγRII (CD32) as a medicament. It has been found that young granulocytes as defined herein above predominantly display the activation epitope recognized by the phage antibody A17. A binding molecule specific for the activation epitope on FcγRII (CD32) that is recognized by the phage antibody A17 is thus preferably used as a medicament, or used for the preparation of a medicament for dampening, reducing and/or preventing an antigen specific immune response or inflammation in an individual. This epitope is also preferably used for the collection of these cells for use in stimulating an immune response. It has been found that old hypersegmented granulocytes as defined herein above predominantly display the activation epitope recognized by the phage antibody A27. A binding molecule specific for the activation epitope on FcγRII (CD32)

that is recognized by the phage antibody A27 is thus preferably used as a medicament, or used for the preparation of a medicament for enhancing, stimulating and/or inducing an antigen specific immune response or inflammation in an individual. This epitope is also preferably used for the collection of these cells for use in dampening an immune response.

EXAMPLES

Experimental Support

The semisynthetic phage antibody display library of human scFv antibody fragments has been described in detail elsewhere (de Kruif J, Terstappen L, Boel E, Logtenberg T. Rapid selection of cell subpopulation-specific human monoclonal antibodies from a synthetic phage antibody library. Proc Natl Acad Sci USA. 1995 Apr. 25; 92(9):3938-42). Briefly, 49 germline VH genes were fused to semirandomized, synthetic, heavy-chain CDR3 regions, varying in length between 6 and 15 amino acid residues. The resulting products were inserted into phagemid vectors, containing seven different light chains of κ and λ subclasses, resulting in a library of $3.6 \times 10^8$ MoPhabs.
Strategy for the Isolation of Phage Antibodies Directed Against Primed Innate Immune Cells Isolation of phages directed against primed granulocytes was performed as follows. In short, the phage library (about $10^{11}$ phage particles) was precleared with resting/unprimed leukocytes from a nonallergic healthy donor ($70 \times 10^6$ cells in 10 ml PBS in the presence of 1% milk) during 90 min at 4° C. on a rotating wheel to deplete the library from all phages recognizing epitopes present on unprimed cells. Subsequently, the precleared library was mixed with GM-CSF-primed eosinophils ($20 \times 10^6$ cells in 10 ml PBS/1% milk) for 90 min at 4° C. on a rotating wheel. We used eosinophil rather than neutrophils or monocytes, because these latter cells are very sensitive for a specific priming caused by isolation artifacts. By using eosinophils, a better chance was foreseen for obtaining antibodies directed against cytokine-induced priming epitopes. The cell-associated phages were isolated from nonbinding phages via two wash steps and a subsequent centrifugation over isotonic Percoll (d 1.030 g/ml, during 20 min, 1000 g at 4° C.). Phages were eluted from the cells by incubation in 76 mM citric acid, pH 2.5, during 5 min at room temperature. This whole procedure was performed three times. Subsequently, the positive phages were expanded, essentially as described before, and screened for epitopes on primed cells, which are absent on resting/unprimed cells.
In Vitro Study Showing that Phage Antibodies A17 and A27 Specifically Recognize a Priming Epitope Ba/F3 Cells Stably Transfected with FcγRII (CD32).
Monoclonal Phage Antibodies (MoPhab) A17 and A27 recognize FcγRII (CD32) expressed on murine Ba/F3 cells stably transfected with FcγRII (CD32). The MoPhab's A17 and A27 were developed to identify primed innate immune cells in vitro and in vivo (see below). The antibodies recognize primed eosinophils, neutrophils and monocytes primed by cytokines in vitro (see FIG. 1) and by inflammatory processes in vivo (see FIGS. 2-8). However, application of these antibodies in biochemical procedures such as Western Blot analysis proofed to be difficult preventing early definition of the recognized structure on primed cells. The hypothesis was tested that the antibodies would recognize a protein specifically present on all innate immune cells and sensitive for inside-out control. FcγRII fulfilled this requirement and was, therefore, tested in stably transfected Il-3 dependent Ba/F3 cells that retained the negative control module of human FcR's. As can be seen in FIG. 9, parental Ba/F3 cells are not recognized by either A17 or A27. When cells are stably transfected with a cDNA expressing FcγRII all cells are recognized by the antibodies in the presence of mIL-3 (see FIG. 9) Ba/F3 cells stably expressing FcαRI are not recognized by the antibodies. These results show that our antibodies specifically recognize the active confirmation of FcRγII.

Blood samples were stained with fluorescein isothiocyanate (FITC) directly labeled phage antibodies A17 and A27. Monoclonal phage antibodies (MoPhabs) A17 and A27 were diluted 1:10 with PBS:4% milk powder (Wt/vol). This mix at 100 μL was added to whole blood samples of 50 μL each and incubated for 60 minutes on ice. Hereafter, the red cells were lysed in ice-cold isotonic NH$_4$Cl and centrifuged at 1500 rpm for 7 minutes. Pelleted cells were washed and resuspended in ice-cold PBS/1% human serum albumin for analysis. Cells were analyzed in a FACS vantage flow cytometer (Becton & Dickinson, Mountain View, Calif.). Floweytometric evaluation of granulocytes, monocytes and lymphocytes was performed according to their specific side scatter (SSC) and forward scatter characteristics (FSC). (see Luijk B al. Allergy Clin Immunol 2005; 115: 997-1003). The labelling of the cells by monoclonal phage antibodies A17 and A27 identifies cytokine primed cell from non-primed cells. Data from individual experiments are reported as fluorescence intensity in arbitrary units (AU) or summarized as the median channel fluorescence (MCF) of at least 5000 events.

The active confirmation of FcγRII (CD32) recognized by monoclonal phage antibodies (MoPhab) A17 and A27 needs induction by cytokines/chemokines and is irrespective of total expression of the FcγII (CD32). Next the hypothesis was tested whether the induction of the activation epitope on FcγRII (CD32) by cytokines/chemokines was associated with an altered expression of the receptor per se. As can be seen from FIG. 2, the expression of total FcγRII (CD32) is not modulated by activation of human neutrophils with different stimuli. In marked contrast, the expression of the activation of activation epitope on FcγRII (CD32) is dependent on activation of the cells.

The active confirmation of FcγRII (CD32) recognized by monoclonal phage antibodies (MoPhab) A17 and A27 is differentially regulated on different subpopulations of neutrophils. To test whether different subpopulation of neutrophils exist in the peripheral blood normal volunteers were challenged with the strong immune stimulus LPS (an i.v. dose of 2 ng/kg *Escherichia coli* 0:113 lipopolysaccharide (LPS) (van Eijk L T, Nooteboom A, Hendriks T, Sprong T, Netea M G, Smits P, van der Hoeven J G, Pickkers P. Shock. 2006 April; 25(4):358-62.)). This in vivo stimulus induces the occurrence of the three phenotypes of neutrophils in the peripheral blood that are characterized by: 1. young/banded cells (CD62L$^{BRIGHT}$. CD16$^{DIM}$ cells see FIG. 10 panel A), 2 normal cells (CD62L$^{BRIGHT}$. CD16$^{BRIGHT}$ cells see FIG. 10 panel B) and old/hypersegmented cells ((CD62L$^{DIM}$. CD16$^{BRIGHT}$ cells see FIG. 10 panel C). These cells have different functional characteristics: Old hypersegmented cells are very sensitive for the in vivo stimulus characterized by a marked increase in A17, A27, CD11b (see FIG. 11) and CD45 and CD54 (see FIG. 12). Interestingly, the high basal expression of these markers on these cells is accompanied by a marked refractoriness of the cells of the innate immune stimulus fMLP. As can be seen from FIG. 13, the quotient of A27 and A17 on neutrophils before and after in vitro activation is much lower (refractoriness) in hypersegmented cells. This refractoriness is not general as the activation of the respiratory burst by FMLP is higher in these cells compared to normal cells (see FIG. 14).

In marked contrast, young banded cells ($CD16^{DIM}$, $CD62L^{BRIGHT}$) are very sensitive for immune signals which is characterized by an enhanced chemotactic response induced by complement fragment C5a (for experimental details see Schweizer R C, van Kessel-Welmers B A, Warringa R A, Maikoe T, Raaijmakers J A, Lammers J W, Koenderman L. J Leukoc Biol. 1996 March; 59(3):347-56.), when compared to the response of hypersegmented cells (see FIG. 15). In addition, these cells are very sensitive for the innate immune stimulator fMLP as characterized by a very clear upregulation of the activation epitope on CD32 recognized by the antibodies A17 and A27.

Acute systemic inflammation caused by challenge with the innate immune stimulus LPS in normal individuals induces a biphasic systemic inflammatory response. When normal individuals are challenge in vivo with LPS (an i.v. dose of 2 ng/kg *Escherichia coli* 0: 113 lipopolysaccharide (LPS) see for experimental details: van Eijk L T, Nooteboom A, Hendriks T, Sprong T, Netea M G, Smits P, van der Hoeven J G, Pickkers P. Shock. 2006 April; 25(4):358-62.) systemic neutrophils in peripheral blood exhibit a biphasic activation response. Phase 1 induced 30-90 min after challenge is characterized by an acute increase in both A17, A27 and sensitivity for the innate immune stimulus fMLP (see FIG. 16). This phase is followed by a second phase 120-360 min after LPS challenge, which is characterized by an enhanced expression of A27, CD45, CD54 and CD11b. Moreover, this phase is characterized by a suppressed sensitivity for fMLP in the context of induction of A17 and A27 (see FIGS. 12,16,17).

Different Subpopulations of Neutrophils Exhibit Different Immune Modulatory Functions.

Up to recently, granulocytes have mainly be considered as effector cells important in killing of microorganisms and mediators of tissue damage in chronic inflammatory diseases. However, under conditions of generalized activation of the innate immune system these cells are found in lymph nodes of patients who died after septic shock (see FIG. 18). This prompted us to study the different subpopulations of neutrophils in vitro T-cell activation in response to PHA and CD3/CD28. FIG. 19 shows that hypersegmented/old neutrophils are very suppressive for T-cell activation, whereas young cells can activate these cells. These data are consistent with the hypothesis that a feedback loop is initiated through old hypersegmented neutrophils to suppress the overload of innate immune activation. In this respect the cells can be characterized as regulatory neutrophils in analogy to regulatory lymphocytes (T-regs see for recent review Wilczynski J R, Radwan M, Kalinka J. Front Biosci. 2008 Jan. 1; 13:2266-74.). Tissue neutrophils under non-diseased conditions are characterized by a specific phenotype: $A17^{DIM}/A27^{Bright}/CD11b7^{Bright}$. As can be seen from FIG. 20 the small population of neutrophils which are found in the broncho-alveolar lavage of normal control individuals exhibits a unique phenotype: $A17^{DIM}/A27^{Bright}/CD11b7^{Bright}$. Based on this finding it is likely that cells characterized in the peripheral blood with a similar phenotype have picked up signals during transition in the tissues.

Clinical studies on innate immune cells obtained from peripheral blood of normal donors and patients with varying inflammatory disorders showing that preactivation in vivo modulates the expression of activated FcγRII (CD32) on innate immune cells.

Clinical Data Regarding Experiments with Asthma Patients: Blood Sampling and Patient Population Blood was obtained from healthy donors without allergy (from the laboratory staff) and patients with various degrees of allergic asthma. Thirty-eight patients who had mild asthma according to the definition of the Global Initiative for Asthma guidelines were selected from patients attending the outpatient clinic of the University Medical Center, Utrecht, The Netherlands, or via advertisements. All subjects had a history of episodic wheezing and periods of impaired lung function (Table I). Twenty-two of these patients with asthma underwent an inhaled allergen challenge according to a standardized protocol in order to document the phenotype of asthma that is characterized by both allergen-induced early and late phase asthmatic reaction. Healthy controls were selected from the laboratory and clinical staff without a history of asthma or presence of atopy (exclusion of atopics was performed by skin prick testing for common allergens). The study was approved by the hospital ethical committee of the University Medical Center, and all patients and healthy controls gave their written informed consent.

Characteristics of patients with asthma (n=38) from whom whole blood was collected (A) and from the subpopulation of this group (n=22) who underwent an inhaled allergen challenge with a late asthmatic response (B)

| | Controls Mean (SD) | A Mean (SD) | B Mean (SD) |
|---|---|---|---|
| Age, y | 31 (5.6) | 22 (5.6) | 22 (5.5) |
| Gender (M/F) | 22/16 | 26/12 | 16/6 |
| Atopy | − | + | + |
| Baseline $FEV_1$ (% predicted) | 101 (2.5) | 94 (10) | 91 (10) |
| Methacholine $PC_{20}$* | — | — | 0.52 (0.07-4.43) |
| Late asthmatic response (% fall in $FEV_1$) | — | — | 30 (10) |
| Allergen† | — | — | 17 House dust mite 2 Cat 3 Grass |

*Geometric mean (range).
†Inhaled allergen during challenge.

Eosinophils are specifically activated in the peripheral blood of stable allergic asthmatics. As can be seen from FIG. 3, eosinophils in the peripheral blood of allergic asthmatics are in marked contrast to neutrophils (and monocytes not shown) characterized by the expression of an activated FcγRII (CD32). Allergen challenge leads to acute (6 hrs after challenge) expression of the A17 epitope on eosinophils, whereas the A27 epitope on eosinophils is not induced (see FIG. 21). These data are proof-of-principle that allergic inflammation is associated with a specific activation pattern of innate immune cells in the peripheral blood. Interestingly, the degree of local inflammation in such stable asthmatics as exemplified by exhaled NO as well as bronchial hyperresponsiveness correlates with the expression of the activated form of FcγRII (CD32) on human eosinophils, which is characterized by recognition of A27 (see FIG. 4). Similar findings were not found with A17.

Neutrophils are Specifically Activated in the Peripheral Blood of a Subtype of Allergic Asthma that is Refractory to Treatment with Glucocorticosteroids.

10-15% of all asthmatics are characterized by a difficult-to-treat phenotype. This phenotype is characterized by the fact that it is impaired sensitive for current anti-inflammatory therapy namely gluco-corticosteroids. This asthma phenotype can be distinguished from normal responsive asthma by the presence of primed neutrophils (A17 and A27) in the peripheral blood (see FIG. 22). The presence of primed neutrophils poorly responsive to steroids) and absence of primed eosinophils (responsive to corticosteroids) can, therefore, be used to diagnose this relatively rare phenotype with a single blood test utilizing the antibodies directed against active FcγRII (A17 and A27). This allows to better define and develop treatment for this inflammatory condition.

Clinical Data Regarding Experiments with Blood of "Healthy Smokers":

Next it was tested whether other inflammatory signatures could be found on innate immune cells under different inflammatory conditions. It was found that smoking by otherwise healthy individuals reflected itself by an activation of monocytes in the peripheral blood. As can be seen from FIG. 5, in marked contrast to the situation with allergic asthmatics, smoking is associated with a distinct inflammatory signature characterized by a specific upregulation of the activated FcγRII (CD32) on monocytes. As can be seen from FIG. 5 neither neutrohils nor eosinophils are activated under these conditions.

Clinical Data Regarding Experiments with Patients with Varying Degrees of RSV Induced Disease:

Comparable to the situation chronic stable diseases also acute inflammation is associated with specific inflammatory signatures. In young patients with RSV induced lower respiratory tract disease a clear eosinophil priming is seen associated with the expression of the active form of FcγRII (CD32) (see FIG. 6). The extend of expression of FcγRII (CD32) on eosinophils is comparable with the situation found in stable allergic asthma. Again more severe disease is associated with enhanced expression of the activation epitope of FcγRII (CD32)

Patients: Infants under 2 years of age, admitted to the hospital with RSV-induced lower respiratory tract infection, were enrolled during two winter epidemics. The diagnosis of RSV LRTD was based on: (1) the presence of a positive immunofluorescence test for RSV on nasopharyngeal secretions; (2) first-ever episode of wheezing; and (3) a paediatrician made a clinical diagnosis of RSV-LRTD with fine crackles, wheze and/or ronchi present on auscultation of their lungs.

In 51 patients and 10 healthy controls, eosinophil activation markers were measured. Children with pre-existing wheezing, chronic lung disease, congenital heart disease or immunodeficiency were excluded from the study. Standard care patients were enrolled from five different small regional hospitals and intensive care patients from the University Medical Centre in Utrecht (UMCU), whereas all blood tests were performed at the laboratory of pulmonary diseases at the UMCU. The study was approved by the Central Committee on Research Involving Human Subjects of the Ministry of Health and the Medical Ethical Committees in all participating centres. Both written and oral permission were obtained from parents or guardians from all patients. To evaluate the disease severity, duration of hospitalization, number of days on supplemental oxygen support and duration of mechanical ventilation were recorded.

Control patients were enrolled at the Urology Department of Paediatrics. Only patients under 2 years of age, undergoing small urological operations without a history of allergy, LRTD or wheezing, were included. None of these patients had a current or recent (urinary tract) infection or were known to have any kind of immunodeficiency.

Clinical Data Regarding Experiments with Patients with COPD:

COPD is associated with a more mixed inflammatory signature induced by smoking (monocytic expression of active FcγRII (CD32)) and chronic pulmonary inflammation (neutrophilic expression of active FcγII (CD32)). When COPD patients are stable and smoke the amount of inflammation correlates with the disease severity as measured by lung function (by forced expiratory volume in 1 second/method known to the art). This was not seen for neutrophils and eosinophils (see FIG. 7). When the patients are admitted the hospital during acute worsening of their disease (exacerbation) the expression of FCγRII (CD32) is high on both monocytes and their peripheral blood neutrophils. This expression decreases during optimal treatment of these patients (see FIG. 23).

COPD patients. Ten patients with unstable moderate to very severe COPD were selected from our outpatient clinic population (Departments of Pulmonary Diseases, Heart & Lung Center Utrecht) when they suffered from a severe exacerbation requiring hospitalization. The patients had to have a smoking history of at least 10 pack years and they fulfilled the criteria for the diagnosis of moderate to very severe COPD according to the GOLD guidelines. At the time of hospitalization they suffered from two or all three of the following symptoms: an increase from baseline of sputum production, sputum purulence or shortness of breath, and they were unresponsive to outpatient therapy. The exacerbations were not life-threatening and did not need intensive care unit management. Patients were allowed to use glucocorticosteroids (GCS) and bronchodilators at admission. Patients with uncontrolled severe diseases other than COPD contributing to the deterioration were excluded. At inclusion before the start of treatment, at the third or fourth day and at day 7 of the treatment period a lung function was performed, the Borg score was reported by the patient (0=no dyspnea to 10=maximum dyspnea), exhaled breath condensate was collected and blood samples were drawn. The subjects were treated according to the ERS guidelines on COPD. In short, GCS (Di-Adreson-F aquosum) was administered intravenously, 50 mg 24 $h^{-1}$ which was tapered to 25 mg 24 $h^{-1}$ after 3-4 days. Oxygen given through a nasal canula was titrated to reach a PaO2 of 8.0 kPa or more, without the occurrence of hypercapnia. Physiotherapy was applied to improve clearance of secretions and to control breathing patterns. Current smokers refrained from smoking during admission. All subjects gave written informed consent to be included in the study, which was approved by the local Ethics Committee.

Clinical Data Regarding Experiments with Patients with Multiple Trauma:

Acute severe systemic inflammation is associated with a phenotype of neutrophils that is refractory to activation in the context of expression of active FcγRII (CD32)). When patients are admitted to the hospital with acute (multiple) trauma expression of active FcγRII (CD32) on neutrophils is only moderately enhanced (see FIG. 24). This inflammatory condition is characterized by a unique inflammatory signature characterized by the fact that innate immune cells are refractory to activation in the context of expression of active FcγRII (CD32) on neutrophils. As can be seen from FIG. 25, the extend of refractoriness of neutrophils is associated with the severity of multi-trauma.

Patients: Thirteen traumapatients (Injury Severity Score [ISS]>16) admitted at the Department of Traumatology, University Medical Center Utrecht, were included in this study (Table 1). The mean ISS was 22.8 (range 16-38) The patients were all males with a mean age of 41.3 (range 20-78). The APACHE II score was determined on a daily basis. The mean APACHE II score was 6.0 (range 0-22) and all infectious complications were registered. Three patients died as a result of severe head trauma and one patient as a result of cardiac arrest caused by myocardial contusion. All four patients died between day 2 and 4 after admittance. The local ethical committee approved the study and informed consent was obtained from all patients or their spouses, in accordance to the protocol.

TABLE 1

Trauma patients characteristics

| | |
|---|---|
| Number of patients | 13 |
| Median age (years) | 40 |
| Age range (years) | 20-78 |
| Gender | |
| Men | 13 |
| Woman | 0 |
| Location of injury | |
| Head | 6 |
| Face | 4 |
| Chest | 10 |
| Abdomen | 4 |
| Extremities | 5 |
| Injury mechanism | |
| Traffic accident | 6 |
| Fall | 6 |
| Weapon | 1 |
| Median Injury Severity Score | 21 |
| ISS range | 16-38 |

Sampling

The day of injury was defined as day 0. Blood samples were taken at admittance, day 1 and every other day during the first week after trauma. This timing of sampling was chosen based on findings in other studies, in which priming (oxidative burst) was most increased between day 2 and 5 after trauma. A lung aspiration was acquired via a non-directed bronchoalveolar lavage (ND-BAL), which is standard of care at the intensive care unit. The results were compared with the expression profile of A17 and A27 on neutrophils in the peripheral blood. Eleven healthy adults (mean age 25±3 years) provided blood samples that served as controls.

Dose response relation between amount of trauma and the systemic innate immune status of trauma patients.

Patients

Two cohorts of patients were included. The first cohort was used to identify relevant PMN surface receptors (see below) and to identify a PMN receptor profile that is associated with the severity of inflammatory reaction of the host to trauma. The second cohort was used to validate this alleged inflammatory score. Ten healthy volunteers served as a control group.

In the first cohort, fifty-two trauma patients with a wide range of severity of their injuries, admitted to the Department of Trauma, University Medical Center Utrecht were included. A wide spectrum of injury severity was chosen to elucidate the range of PMN receptor expression profile.

In the second cohort, thirty-one trauma patients who required intensive care admission were included. ICU admission was added to the inclusion criteria, as this is the patient population of interest: patients most at risk for complications (e.g. ALI or ARDS).

For both cohorts, exclusion criteria were age <16 years or >80 years and patients with an altered immunological status (e.g. corticosteroid use or chemotherapy). A blood sample was taken prior to any surgical procedure and within 24 hours after admission. The local ethical committee approved the study and written informed consent was obtained from all patients or their legal representatives in accordance with the protocol.

Clinical Parameters

Injury Severity Score (ISS) and APACHE II Score were calculated on admission (Baker S P, O'Neill B, Haddon W, Jr., et al. The injury severity score: a method for describing patients with multiple injuries and evaluating emergency care. J. Trauma. 1974; 14(3)187-196.; Knaus W A, Draper E A, Wagner D P, et al. APACHE II: a severity of disease classification system. Crit Care Med. 1985; 13(10)818-829). Within the first 72 hours after injury (maximal 48 hours after sampling), presence of systemic inflammation (i.e. systemic inflammatory response syndrome [SIRS]), or the occurrence of pulmonary complications (e.g. acute lung injury [ALI], or acute respiratory distress syndrome [ARDS]) were assessed in the first cohort according their clinical criteria as determined in the consensus conferences for SIRS and ARDS (Bernard G. R., Artigas A, Brigham K. L. The American-European consensus conference on ARDS. Am. J. Respir. Crit Care Med. 1994; 149818-824. Levy M M, Fink M P, Marshall J C, et al. 2001 SCCM/ESICM/ACCP/ATS/SIS International Sepsis Definitions Conference. Crit Care Med. 2003; 31(4)1250-1256). The presence of pneumonia was determined by a positive sputum culture, an infiltrate on the chest X-ray and clinical symptoms of infection (Adams J M, Hauser C J, Livingston D H, et al. Early trauma polymorphonuclear neutrophil responses to chemokines are associated with development of sepsis, pneumonia, and organ failure. J. Trauma. 2001; 51(3)452-456). Pulmonary problems due to cardiac failure were measured by chest X-ray, high venous pressure (as determined by Swahn-Ganz catheter) and clinical signs of cardiac pump failure. Transfusion related data and intensive care support days were recorded.

Materials

For analysis of PMN receptor expression by flowcytometry the following monoclonal antibodies were commercially purchased: FITC-labeled IgG1 negative control (clone DD7, Chemicon, Hampshire, United Kingdom), RPE-labeled IgG2a negative control (clone MRC OX-34, Serotec, Dusseldorf, Germany), RPE-labeled CD11b (clone 2LPM19c, DAKO, Glostrup, Denmark), FITC-labeled CD16 (clone LNK16, Serotec, Dusseldorf, Germany), RPE-labeled CD32 (clone FLI8.26, BD Pharmingen, Franklin Lakes, United States), FITC-labeled CD62L (clone Dreg-56, BD Pharmingen, Franklin Lakes, United States), FITC-labeled CD88 (clone W17/1, Serotec, Dusseldorf, Germany), FITC-labeled CD181 (clone 42705, R&D Systems, McKinley Place, Minn.) and RPE-labeled CD182 (clone 48311, R&D Systems, McKinley Place, Minn.). Two FITC-labeled monoclonal phage antibodies, which recognize an activated Fcγ-receptor complex, were manufactured at the Department of Respiratory Medicine at the University Medical Center Utrecht (MoPhaps A17 and A27, UMCU, Utrecht, The Netherlands) [17, 18]. Interleukin 6 (IL-6) was measured by ELISA (Pierce Biotechnology Inc., IL, United States) as described by the manufacturer. Hematology parameters were determined at the Clinical Laboratory Department of the University Medical Center Utrecht.

PMN Activation Status

The inflammatory status of PMNs can be assessed by functional analysis, such as measurement of radical oxygen species (ROS). In this study multiple, well documented PMN receptors were analyzed in relation to systemic inflammation induced by tissue injury to identify an inflammation associated receptor profile which could determine the inflammatory state of the individual patient.

Blood was collected in a Vacutainer® with sodium heparin as anticoagulant cooled immediately and kept on ice during the whole staining procedure. The analysis of the PMN receptor expression was started within two hours after the blood sample was obtained. The expression of the above mentioned markers was measured. The expression of active FCγRII (CD32) was also measured after 5 minutes of stimulation of whole blood at 37° C. with N-formyl-methionyl-leucyl-phenylalanine (fMLP $10^{-6}$M) to evaluate the responsiveness of the cells for a bacterial derived activating agonist as a measure of maximal activation. After stimulation, the samples were put on ice again and analyzed.

Blood samples were stained with fluorescein isothiocyanate (FITC) directly labeled phage antibodies A17 and A27 as described previously and the commercial markers as described by their manufacturer. In short, the directly labeled antibodies were added 1:20 to whole blood and incubated for 60 minutes on ice. After incubation, the red cells were lysed with ice-cold isotonic $NH_4Cl$. After a final wash with PBS2+ (phosphate buffered saline with added sodiumcitrate and pasteurized plasma proteins), the cells were analyzed in a FACScalibur Flowcytometer (Becton & Dickenson, Mountain View. CA). The PMNs were identified according to their specific side-scatter and forward-scatter signals. Data from individual experiments are depicted as fluorescence intensity in arbitrary units (AU) or summarized as the median channel fluorescence (MCF) of at least 10000 events.

From Inflammatory Profile to Inflammatory Score

For all measured receptors, the minimum and maximum relative expression levels were determined. Then the correlation between individual PMN receptor expression and injury severity (ISS) was determined. The PMN receptors which showed significant correlation with the ISS (CD11b and $A27_{fMLP}$) were combined to create a clinically useable inflammatory score.

First, the 95%-CI levels of the expression were determined for both receptors: the confidence interval of CD11b expression was 100 to 1000 mean fluorescence units (MFU), whereas the confidence interval of $A27_{fMLP}$ was 300 to 10000 MFU. These ranges were transformed into a 5 point scale. The extent of decreased $A27_{fMLP}$ expression and the extent of increased CD11b expression were added together forming an inflammatory scale of 0-10, with 0 representing no inflammation and 10 representing maximal inflammation.

IL-6 Analysis

Blood was collected in a Vacutainer® with EDTA as anticoagulant, cooled immediately and kept on ice during the procedure. Plasma was isolated by spinning the sample down at 1000 G. IL-6 was determined using a human IL-6 sandwich ELISA (Endogen, Pierce Biotechnology, IL, United States) according to the procedures prescribed by the manufacturer.

Statistics

Results are expressed as means±standard error of mean (SEM). Statistical analysis was performed with the non-parametric Mann-Whitney U test to compare groups. Pearson correlation analysis was performed for comparison of two continues variables. Statistical significance was defined as $p<0.05$.

Patient Demographics

In the first cohort of 52 patients the mean age was 38 (SD=20) and the mean ISS was 11 (SD=9). In the second cohort of 31 patients the mean age was 40 (SD=17) and the mean ISS was 25 (SD=11). Demographics are summarized in Table 1.

TABLE 1

Patient demographics

| | Cohort 1 (Mean ± SD) | Cohort 2 (Mean ± SD) |
|---|---|---|
| Number of patients (n) | 52 | 31 |
| Male/Female (n) | 31/21 | 25/6 |
| Age (years) | 38 (20) | 40 (17) |
| Injury Severity Score | 11 (9) | 25 (11) |
| APACHE II Score | 4 (6) | 13 (7) |
| Time to sampling (<12 hrs/12-24 hrs) | 35/17 | 14/17 |
| Time on ICU (days) | 2.5 (6.1) | 15 (12.8) |
| Time on ventilation (days) | 2.2 (5.6) | 14 (13.0) |
| Packed red blood cells before sampling (units) | 0.7 (1.3) | 3.1 (5.6) |
| Fresh frozen plasma before sampling (units) | 0.2 (0.9) | 1.3 (2.9) |
| Cause of trauma (n) | | |
| MVA | 36 | 22 |
| Assault | 0 | 1 |
| Fall of height | 15 | 6 |
| Penetrating trauma | 1 | 2 |
| Complications (n) | | |
| None | 33 | NA |
| Cardiac failure | 3 | |
| SIRS | 9 | |
| Pneumonia | 2 | |
| ALI/ARDS | 5 | |

Identification of Relevant PMN Surface Receptors

In the first cohort 10 PMN surface markers, which expressions are modulated by activation, were analyzed in relation to injury severity (ISS). Most PMN surface receptors (8/10) did not correlate with the magnitude of trauma. All 8 receptors showed decreased expression when injury severity increased. However, no relation was found between the extent of expression and the severity of trauma. Therefore, these were excluded for further analysis and were not validated in the second cohort. Expression of the alpha chain of Mac-1 (CD11b) and activated FcγRII (CD32) recognized by A27 after stimulation with fMLP ($A27_{fMLP}$) were statistically significant correlated with injury severity (Table 2).

P79245PC00

TABLE 2

Individual PMN surface receptor expression correlation with injury severity.

| Cohort 1 | A17 | A27 | CD11b | CD16 | CD32 | CD62L | CD88 | CD181 | CD182 | $A27_{fMLP}$ |
|---|---|---|---|---|---|---|---|---|---|---|
| ISS (p-value) | 0.558 | 0.130 | 0.038 | 0.614 | 0.261 | 0.489 | 0.161 | 0.299 | 0.139 | 0.001 |
| Pearson correlation | | | $r^2$ = 0.094 | | | | | | | $r^2$ = 0.226 |

The pattern of correlation differed for the 2 markers. $A27_{fMLP}$ decreased after injury, with a maximal decline in the lower injury scores. CD11b increased after injury, with a maximal increase in the higher injury scores (FIG. 26).

Inflammation Score Based on PMN Phenotype

To combine CD11b and A27$_{fMLP}$ in an inflammatory score, their scales were altered to a 5 point scale as described in the methods section. Because A27$_{fMLP}$ was inversely correlated, 5 points were attributed to the lowest relative expression. Relative CD11b expression was maximized at 5 points for outliers above the 95%-CI to maintain equal input of both receptors to the inflammatory score. Both receptors were combined to form an inflammatory score ranging from 0-10 points. The resulting inflammatory score was significantly correlated with the injury severity score, with a p-value of 0.000 and an $r^2$ of 0.337.

Validation of the Inflammatory Score in a Second Cohort

In the second smaller cohort single expression values of CD11b and A27$_{fMLP}$ were not statistically significant correlated with the ISS (p=0.215 and p=0.062 respectively). However, the inflammatory score was statistically significant correlated with the ISS in this more severely injured population, with a p-value of 0.040 and an $r^2$ of 0.147. The inflammatory score based on early phenotype changes after trauma showed a better correlation with the ISS for the blood samples taken within 12 hours after trauma (with a correlation coefficient of $r^2$=0.277).

Complications and the Inflammatory Score

Change in PMN phenotype is thought to be related to the development of inflammatory complications such as ALI and ARDS. Therefore, patients were analyzed regarding their inflammatory score and the development of complications within the first 48 hours after sampling. In the first cohort, two patients (age >70) developed pleural fluid as a result of cardiac failure after minor trauma and subsequent surgery, two patients developed ALI and four patients fulfilled the ARDS criteria. Five patients developed pneumonia and nine patients fulfilled the SIRS criteria, though developed no further complications. The newly formed inflammatory score increased when the severity of inflammatory pulmonary complications increased (FIG. 27). The highest inflammatory score was found in patients who developed ALI or ARDS, the lowest score was found in patients without signs of inflammation and the three older patients with cardiac failure (no complications versus ALI/ARDS p=0.001 by Mann Whitney U analysis).

Biphasic Inflammatory Reaction after Trauma: the Initial Inflammatory Response Predicts Late Phase Septic Shock Patients A consecutive series of surgical intensive care patients in the University Medical Centre Utrecht were included. Patients were between 18 and 80 years old, with an expected ICU stay of >3 days. Exclusion criteria were chronic disease influencing the immune system and the use of immunosuppressive medication. The patients were followed for 14 days or as long as their stay on the ICU lasted. Informed consent was obtained as soon as possible from the patient self or by a legal representative. The local ethical committee approved the study and written informed consent was obtained from all patients or their legal representatives in accordance with the protocol.

Clinical Parameters

The APACHE-II score was calculated on admission (Knaus W A, Draper E A, Wagner D P, et al. APACHE II: a severity of disease classification system. Crit Care Med. 1985; 13(10)818-829)). Criteria for SIRS (Systemic Inflammatory Response Syndrome), sepsis or septic shock as defined by the criteria proposed by the International Sepsis Definitions Conference were assessed on a daily basis (Baker S P, O'Neill B, Haddon W, Jr., Long W B. The injury severity score: a method for describing patients with multiple injuries and evaluating emergency care. J Trauma 1974; 14(3):187-196.).

Sampling

A first blood sample was taken within the first 12 hours after the patients' admission to the ICU (day zero). Serial blood samples were taken on a daily basis during the next 14 days of the patients' admission. Blood was collected in a Vacutainer® with sodium heparin as anticoagulant cooled immediately and kept on ice during the whole staining procedure, which started directly.

Materials

For analysis of PMN receptor expression by flowcytometry the following monoclonal antibodies were commercially purchased: FITC-labeled IgG1 negative control (clone DD7) from Chemicon, Hampshire, United Kingdom; RPE-labeled IgG2a negative control (clone MRC OX-34), FITC-labeled CD16 (clone LNK16) and FITC-labeled CD88 (clone W17/1) from Serotec, Dusseldorf, Germany; RPE-labeled CD11b (clone 2LPM19c) from DAKO, Glostrup, Denmark; RPE-labeled CD32 (clone FLI8.26) from BD Pharmingan, Franklin Lakes, United States; FITC-labeled CD181 (clone 42705) and RPE-labeled CD182 (clone 48311) from R&D Systems, McKinley Place, Minn. A monoclonal phage antibody, which recognizes an activated FcγRII (active CD32), was manufactured at the Department of Respiratory Medicine at the University Medical Center Utrecht (MoPhaps A27, UMCU, Utrecht, The Netherlands) (18; 19). Interleukin 6 (IL-6) analysis was performed using a sandwich ELISA (Pierce Biotechnology Inc., IL, United States) as described by the manufacturer.

Flowcytometer Analysis

The inducible expression of active FcγRII (CD32) was measured after 5 minutes of stimulation of whole blood at 37° C. with N-formyl-methionyl-leucyl-phenylalanine (FMLP $10^{-6}$M) to evaluate the responsiveness of the cells for a bacterial derived activating agonist as a measure of maximal activation. After stimulation, the samples were put on ice again and analyzed.

Blood samples were stained with directly labeled antibodies. In short, the directly labeled antibodies were added 1:20 to whole blood and incubated for 60 minutes on ice. After incubation, the red cells were lysed with ice-cold isotonic $NH_4Cl$. After a final wash with PBS2+ (phosphate buffered saline with added sodiumcitrate and pasteurized plasma proteins), the cells were analyzed in a FACScalibur Flowcytometer (Becton & Dickenson, Mountain view. CA). The PMNs were identified according to their specific side-scatter and forward-scatter signals. Data from individual experiments are depicted as fluorescence intensity in arbitrary units (AU) or summarized as the median channel fluorescence (MCF) of at least 10000 events.

Determination of the Respiratory Burst

Two milliliter of whole blood was lysed with 10 ml isotonic $NH_4Cl$, as described previously, and the pellet was washed with PBS2+ (20). Cells were counted in a Cell-Dyn 1800 hematology cell analyzer (Abbott diagnostics, Illinois USA) and resuspended in incubation buffer (20 mM HEPES, 132 mM NaCl, 6.0 mM KCl, 1.0 mM $MgSO_4$, 1.2 mM $KH_2PO_4$, supplemented with 5 mM glucose, 1.0 mM $CaCl_2$, and 0.5% (w/v) HSA) at a concentration of 106 PMNs per ml. Fifty μl of cell suspension was added to 100 μl reaction mix (12.5 μl of 20 mM Amplex Red in DMSO and 25 μl of 200 U/ml HRP in PBS, diluted in a total of 5 ml of HEPES 3+), in a white 96 wells plate (Microplate, Labsystems, Helsinki, Finland). Cells were stimulated with 50 μl of HEPES 3+ (negative control), Phorbol myristate acetate (PMA) ($10^{-6}$), fMLP ($10^{-6}$) or PAF/fMLP (both $10^{-6}$) and directly analyzed in a FLUOstar OPTIMA microplate reader (BMG Labtech, Germany) to measure radical oxygen species production. The cells were analyzed every 30 seconds for 30 minutes at 37° C., undergoing intermittent shaking of the plate.

IL-6 Analysis

Blood was collected in a Vacutainer® with EDTA as anticoagulant, cooled immediately and kept on ice during the procedure. Plasma was isolated by spinning the sample down at 1000 G. IL-6 was determined using a human IL-6 sandwich ELISA according to the procedures prescribed by the manufacturer.

Statistics

Results in figures are generally expressed as means±standard error of mean (SEM). Statistical analysis was performed with the non-parametric Mann-Whitney U test to compare groups. The predictive value of expression of inducible active FcγRII ($A27_{fMLP}$) was calculated using a Receiver Operating Curve analysis. Statistical significance was defined as $p<0.05$.

Results

Demographics

Forty-one patients admitted to the ICU department were analyzed. Thirty-six patients were admitted after (multi) trauma, the other 5 were post-operative patients. Thirty-five of the included patients developed a SIRS, 24 patients met the sepsis criteria and 12 patients developed septic shock (17). All trauma patients that developed septic shock (n=10) fulfilled the septic shock criteria between days 8-10 after admission. One post-operative patient developed septic shock on the second day, the other on the seventh day of ICU admission. Four patients died during their admission, one of whom died during the study period. Causes of death were multiple organ failure for 3 patients and cardiac arrest for 1 (table 1).

Admission Severity and Events

No relation could be found between the development of sepsis and the admission APACHE-II score (Mann Whitney U test p=0.090). The APACHE-II score was increased in patients who developed septic shock (mean 18.9±7.6 SD) as compared to patients without septic shock (mean 13.1±7.1 SD) by Mann Whitney U test (p=0.029).

Systemic Inflammation Reflected by PMN Phenotype

The PMNs of patients who developed septic shock were characterized by an initial hyper-responsive phenotype in the context of respiratory burst. This is illustrated by elevation of the spontaneous ROS production in the absence of a stimulator (p-value <0.05 during days 0-4). PMA, fMLP and PAF/fMLP triggered ROS production was not significantly altered during admission. In the ensuing days, the increased spontaneous ROS production returned to slightly above control levels.

The expression of CD11b on admission was significantly increased as compared to controls (p=0.003), but no significant difference was found between patients who developed septic shock and patients who did not. After a gradual decrease towards normalization, a second increase in CD11b expression was seen after the onset of septic shock (FIG. 28A)

The chemotaxis associated receptors CD181 and CD182 (IL-8R's) and the opsonin receptor CD16 (FcγRIIIB) were significantly decreased in all patients as compared to controls throughout the study period.

On admission, the complement receptor CD88 (C5aR) and opsonin receptor CD32 (FcγRII) were significantly decreased in patients with septic shock as compared to controls (p=0.005 and p=0.008 respectively). However, no significant difference was found between patients with septic shock in the study period and patients who did not develop septic shock (FIGS. 28B and 28C). Both CD88 and CD32 showed a gradual decrease starting from day 1 with their lowest expression between 6-8 days after admission, just prior to clinical signs of septic shock. Throughout the first week, expression was consistently lower (although not statistically significant) in patients who developed septic shock. During the study period all patients showed a lasting decreased expression of PMN surface receptors.

A statistically significant decrease in active FcγRII after fMLP stimulation ($A27_{fMLP}$) was seen in the septic shock group within the first 12 hours of admission, compared to the expression in non-septic shock patients. This decreased expression returned to the levels comparable to non septic-shock patients the next day (FIG. 28 D). From days 1-6 a similar trend as for CD88 and CD32 was seen, the lowest expression levels were found between 6-8 days.

Predictive Value of FMLP Induced Expression of Active FcγRII ($A27_{fMLP}$)

Within 12 hours after the injury, fMLP induced expression of active FcγRII ($A27_{fMLP}$) showed a striking difference between patients that developed septic shock after a period of 8 (!) days and those who did not. The A27 mLP expression plotted in a receiver operating curve (ROC) against septic shock showed an area under the curve of 0.869 and a significance of p=0.009. The optimum cut-off point for $A27_{fMLP}$ was at 25% of control levels (100% sensitivity and 75% specificity). In comparison, initial plasma IL-6 concentrations did not show a significant predictive value (area under the curve of 0.764 and a p-value of 0.071) (see FIG. 29).

P79245PC00

Long term activation of the innate immune system leads to exhaustion of effective immunity against microorganisms: important cause of late onset (8-12 days) of sepsis and septic shock after trauma. Multi-organ failure after late septic shock after trauma is characterized by massive homing of neutrophils to a variety of tissues including lung, spleen, and lymph nodes (see FIG. 18). These cells exhibit a unique phenotype characterized by a unique expression of cell surface markers (see table below).

| Ptn | A17 | A27 | CD16 | CD32 | CD62L | A17fMLP | A27fMLP | CD49d (%) |
|---|---|---|---|---|---|---|---|---|
| Control | 89 | 102 | 797 | 300 | 314 | 8540 | 10000 | 2 |
| Sepsis | 43 | 39 | 201 | 113 | 113 | 403 | 1161 | 37 |
| Lungfluid | 4947 | 2913 | 853 | 956 | 31 | 4858 | 2987 | 25 |
| Chylus | 3436 | 5749 | 1285 | 565 | 73 | 6702 | 5999 | 32 |

Particularly, the expression of VLA-4 and extreme expressions of A17 and A27 are induced under these conditions and it is likely that this adhesion molecule is necessary for homing of the neutrophils from tissues to the spleen. These cells are characterized by a functional VLA-4 receptor as the cells avidly bind to the VIA-4 ligand VCAM-1 coated beads (see FIG. 30). Interestingly, these cells have a marked impaired responsiveness towards FMLP, PMA and PAF/FMLP indicating that the cells are paralyzed in terms of cytotoxic functions (see FIG. 31). These cells are a sign of an exhausted immune system. Under these conditions patients are at extreme risk for infectious complications.

In Summary.

The innate immune response after trauma is an essential for the host defense against tissue injury and the combat against invading organisms. However, when this response is activated either too pronounced and/or too long the same system mediates the systemic damage to host tissues. Depending on the state of the immune system, immunity should be boosted or antagonized. The current invention makes it possible to both diagnose the type and extend of the innate immune response and can be utilized to actively interfere with this immune response (see FIG. 32)

The invention claimed is:

1. A method for estimating a risk of complications in an individual that has suffered a trauma comprising determining in a blood sample obtained from said individual within 24 hours after suffering said trauma the level of an activation epitope wherein said activation epitope is an epitope recognized by phage antibodies A17 and/or A27 deposited at Centraal Bureau voor Schimmelcultures as CBS120667 and CBS120668, respectively, of the FcγRII (CD32) receptor on blood cells of said individual, wherein said determining comprises contacting said sample with a binding molecule for said activation epitope, and wherein a decreased level of said epitope indicates an increased risk of complications.

2. The method of claim 1, which further comprises determining the level of Mac-1 (CD11b) receptor, wherein a high level of CD11b receptor and a low level of CD32 receptor indicates an increased risk of complications.

3. The method of claim 1, wherein said complication comprises a pulmonary complication or septic shock.

4. The method of claim 1, wherein said blood sample is obtained from said individual within 12 hours after suffering said trauma.

* * * * *

UNITED STATES PATENT AND TRADEMARK OFFICE
CERTIFICATE OF CORRECTION

PATENT NO. : 8,460,883 B2
APPLICATION NO. : 12/520852
DATED : June 11, 2013
INVENTOR(S) : Koenderman et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 648 days.

Signed and Sealed this
Eighth Day of September, 2015

Michelle K. Lee
*Director of the United States Patent and Trademark Office*